(12) United States Patent
Redda et al.

(10) Patent No.: US 8,314,143 B2
(45) Date of Patent: Nov. 20, 2012

(54) SYNTHETIC FLAVONOIDS AND PHARMACEUTICAL COMPOSITIONS AND THERAPEUTIC METHODS OF TREATMENT OF HIV INFECTION AND OTHER PATHOLOGIES

(75) Inventors: Kinfe Redda, Tallahassee, FL (US); Chavonda Janeebra Mills, Decatur, GA (US); Nelly Mateeva, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 11/968,146

(22) Filed: Dec. 31, 2007

(65) Prior Publication Data

US 2012/0264820 A1    Oct. 18, 2012

Related U.S. Application Data

(60) Provisional application No. 60/877,623, filed on Dec. 29, 2006.

(51) Int. Cl.
*A61K 31/35* (2006.01)
*A61K 31/12* (2006.01)

(52) U.S. Cl. ........................... 514/456; 514/675

(58) Field of Classification Search .............. 514/456, 514/675
See application file for complete search history.

(56) References Cited

U.S. PATENT DOCUMENTS 5,399,558 A * 3/1995 Baker et al. ............ 514/232.5
5,773,462 A * 6/1998 Lin et al. ................. 514/456

* cited by examiner

*Primary Examiner* — Raymond Henley, III
(74) *Attorney, Agent, or Firm* — Thomas Horstemeyer, LLP

(57) ABSTRACT

A compound, pharmaceutical composition and method for the treatment of mammals wherein the active therapeutic agent is a compound having the structure:

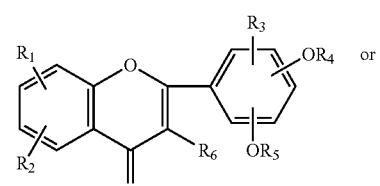

[I]

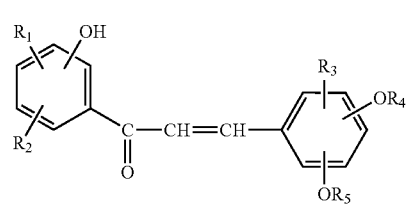

[II]

wherein:
$R_1$ is an electronegative substituent,
$R_2$ is $R_1$ or alkyl,
$R_3$ is H or O-alkyl,
$R_4$ and $R_5$ are the same or different and are alkyl and
$R_6$ is H or OH.

33 Claims, 10 Drawing Sheets

| CODE | Molecular Formula | Structure |
|---|---|---|
| CHCl3M | $C_{18}H_{18}Cl_2O_5$<br>Exact Mass: 382.04<br>Mol Wt: 383.22<br>C, 56.41; H, 4.21; Cl, 18.50; O, 20.87 | |
| CHBr3M | $C_{18}H_{18}Br_2O_5$<br>Exact Mass: 469.94<br>Mol Wt: 472.12<br>C, 45.79; H, 3.42; Br, 33.85; O, 16.94 | |
| CHNM3M | $C_{19}H_{19}NO_7$<br>Exact Mass: 373.12<br>Mol Wt: 373.36<br>C, 61.12; H, 5.13; N, 3.75; O, 30.00 | |
| CHCl2M | $C_{17}H_{14}Cl_2O_4$<br>Exact Mass: 352.03<br>Mol Wt: 353.20<br>C, 57.81; H, 4.00; Cl, 20.08; O, 18.12 | |
| CHBr2M | $C_{17}H_{14}Br_2O_4$<br>Exact Mass: 439.93<br>Mol Wt: 442.10<br>C, 46.18; H, 3.19; Cl, 36.15; O, 14.48 | |
| CHNM2M | $C_{18}H_{17}NO_6$<br>Exact Mass: 343.11<br>Mol Wt: 343.33<br>C, 62.97; H, 4.99; N, 4.08; O, 27.96 | |

| Structure | Molecular Formula | CODE |
|---|---|---|
| (3,4,5-trimethoxyphenyl flavonol with 6,8-diCl) | $C_{18}H_{14}Cl_2O_6$<br>Exact Mass: 396.02<br>Mol Wt: 397.21<br>C, 54.43; H, 3.55; Cl, 17.85; O, 24.17 | FLCl3M |
| (3,4,5-trimethoxyphenyl flavonol with 6,8-diBr) | $C_{18}H_{14}Br_2O_6$<br>Exact Mass: 483.92<br>Mol Wt: 486.11<br>C, 44.47; H, 2.90; Br, 32.87; O, 19.75 | FLBr3M |
| (3,4,5-trimethoxyphenyl flavonol with 6,8-diNO$_2$) | $C_{18}H_{17}NO_8$<br>Exact Mass: 387.10<br>Mol Wt: 387.34<br>C, 58.92; H, 4.42; N, 3.62; O, 33.04 | FLNM3M |
| (3,4-dimethoxyphenyl flavonol with 6,8-diCl) | $C_{17}H_{12}Cl_2O_5$<br>Exact Mass: 366.01<br>Mol Wt: 387.18<br>C, 55.61; H, 3.29; Cl, 19.31; O, 21.79 | FLCl2M |
| (3,4-dimethoxyphenyl flavonol with 6,8-diBr) | $C_{17}H_{12}Br_2O_5$<br>Exact Mass: 453.91<br>Mol Wt: 456.08<br>C, 44.77; H, 2.65; Cl, 35.04; O, 17.54 | FLBr2M |

Fig. 4B

SYNTHETIC FLAVONOIDS AND PHARMACEUTICAL COMPOSITIONS AND THERAPEUTIC METHODS OF TREATMENT OF HIV INFECTION AND OTHER PATHOLOGIES

CROSS-REFERENCE TO RELATED APPLICATIONS

This application claims the benefit of provisional patent application Ser. No. 60/877,623, filed, Dec. 29, 2006; the entire contents and disclosure of which is incorporated herein by reference.

FIELD OF THE INVENTION

The present invention relates to novel therapeutic agents suitable for the treatment of mammals those afflicted with viral and retroviral, in particular, HIV infections.

BACKGROUND OF THE INVENTION

The entire disclosure and content of each reference and patent referred to herein is incorporated by reference.

Flavonoids (benzo-γ-pyrones), as shown in Scheme 1 are a class of about 4,000 natural compounds present in all vascular plants. They appear to exhibit a wide range of biological activities including anti-oxidative [H. Bao et al, Food Chemistry, 86, 517 (2004); T. Miura et al, Food and Chemical Toxicology 41, 759 (2003)], anti-inflammatory [J. J. A. Hendricks et al, Journal of Experimental Medicine, 200,1667 (2004); H. Y. Lin et al, Journal of Cellular Physiology, 202. 579 (2005); Y. S. Chi et al, Biochem. Pharmacol, 62, 1185 (2001)], cancer suppressing [T. Zhang et al, Biorganic & Medicinal Chemistry, 12, 6097 (2004); C. A. Rowe et al, Journal of Medicinal Food, 7,402 (2004). X. Zheng et al, Bioorganic and Medicinal Chemistry Letters, 13, 3423 (2003; X. Zheng et al, Bioorganic and Medicinal Chemisty Letters, 13, 881 (2003)] and antiviral (anti-HIV) [W. Wang et al, Antiviral Research, 64, 189 (2004); T. B. Ng, et al, Life Sei., 61, 933 (1997); A. J. Vlietnick et al, Plant Flavonoids in Biol. And Medicine II: Biochem. Cell. and Medicinal Properties, 283 (1988).]. The average human diet contains about 1 g of flavonoids per day, assimilated through fruits, vegetables, red wine, tea etc. [G. Di Carlo et al, Life Sciences, 65, 337 (1999)].

SCHEME 1

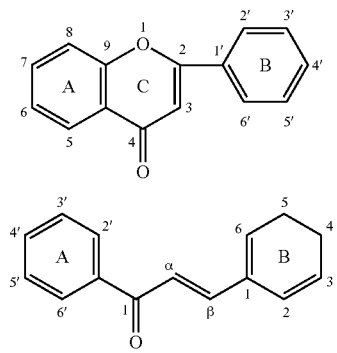

A family of flavonoids are known to be selectively toxic to multidrug resistant cancer cells. Several recent studies have linked the regulation of P-glycoprotein (Pgp) gene expression to the expression of the drug-metabolizing P450 genes, with the speculation that, in normal cells, P-glycoprotein may function in conjunction with the P450 enzymes in the detoxication of xenobiotics. Indeed, benzo[a]pyrene, an inducer and a substrate for cytochrome P4501a1, is also a substrate for P-glycoprotein. While investigating the coordinated regulation of these genes following exposure of multidrug resistant (MDR) cells to inducers of P450 gene expression, it was observed that one of these inducers, β-naphthoflavone (βNF), was considerably more toxic to multidrug resistant cells than to their drug-sensitive counterparts. This collateral sensitivity to βNF and other flavonoid compounds has now been further investigated in several multidrug resistant cell lines. For a further discussion of the anti-cancer properties of flavonoids, see US. H1,427; U.S. Pat. Nos. 5,336,685; 6,706,865 and 6,528,042.

Plant flavonoids usually occur in plants as glycosides, although in some circumstances they may occur as free aglycones. Most glycosides are O-glycosides, with the most common monoglycoside being at the 7-position. Diglycosides usually have sugars at the −7 and −3 positions and occasionally the −7 and −4' positions. Other combinations and monoglycosides exist but are less abundant. C-glycosides also occur in a more restricted distribution with C-6 and C-8 glycosides being the most common.

Plant flavonoids have antioxidative properties, cytostatic effects in tumorigenesis, and the ability to inhibit a broad spectrum of enzymes, such as angiotensin converting enzyme (ACE), protein kinase C, tyrosine protein kinase, and topoisomerase II. They are regarded as potential cancer preventatives and cardioprotective agents. Their potential use as anti-inflammatory or antiviral agents has also been examined. It is also disclosed in the literature that bioflavonoids, especially rutin, citrin, quercetin, hesperidin or derivatives are responsible for the inactivation of protein-cleaving enzymes (such as hyaluronidase and/or collagenase), which promote skin-aging processes. These compounds are used for general skin care or cosmetic surgery. It is reported that rutin, quercetin, isoquercitrin, catechin and other compounds also prevent and ameliorate the aging phenomena of the skin. It is also said that, together, quercetin glycoside, divalent metal ion, and extract of liquorice prevent intoxication by promoting alcohol metabolism in the human liver.

Rutin is a flavonoid glycoside comprised of quercetin and the sugar, rutinose. Many beneficial health effects of rutin have been demonstrated. Such effects have been attributed to anti-inflammatory, anti-mutagenic, anti-tumor, anticarcinogenic, smooth muscle relaxation, and estrogen receptor binding activities of rutin. Rutin is also being used in the treatment of capillary fragility, cerebral thrombosis, retinitis and rheumatic-fever-associated hemorrhagic conditions. Under conditions of low dietary fat intake, rutin and quercetin have been reported to considerably suppress colon tumor incidence. Backhaus (Use of bioflavonoid, especially rutin for retrovirus inactivation. Germany Patent DE4340438) claimed that rutin and its derivatives, in an oral dosage form, and injection or infusion solution, or a suppository, would inactivate retroviruses (e.g., HIV).

Most of the flavonoids have been isolated from plants in order to test their biological properties; others have been synthetically produced in search of more potent drug candidates.

The structure-activity relationship (SAR) in flavonoids is empirical, i.e., based on numerous data from testing different compounds. Although there are a lot of data in the literature, it is very difficult to outline a clear tendency that will lead to an optimized structure of high activity and low toxicity.

Among the most studied compounds, quercetin and baicalin are polyhydroxylated flavones [L. M. Larocca et al, J. Ural., 152, 1029 (1994) 1417; K. Ono et al, Biochem. Biophys. Res. Commun., 160, 982 (1989); B. Q. Li et al, Cell And Mol. Biol. Res., 39, 119 (1993)]. It is believed that the important structural features leading to high biological activities are the presence of 5-OH and 3-OH groups. The latter, however, is considered to be responsible for some mutagenic properties observed in quercetin, which disappeared after this group was methylated. Their solubilities can be modified through selective introduction of lipophilic and hydrophilic substituents. The most popular approach is to balance the number of the alkyl substituents and free hydroxyl groups.

The incorporation of electronegative elements, such as halogens and nitro groups in the flavonoid structure, introduce new patterns of biological properties. 4',6-dichloroflavan has been reported to be a potent antirhinovirus compound. Halogenated and nitro-substituted flavones exhibit structure-dependent aryl hydrocarbon receptor (AhR) agonist and antagonist activities comparable to that observed for 2,3,7,8-tetrachlorodibenzo-p-dioxin (TCDD) [Y. F. Lu et al, Biochemical Pharmacology. 51. 1077 (1996)]. 8-Iodo, 8-bromo, and 8-trifluoromethyl derivatives of chrysin exhibit strong activities against human gastric adenocarcinoma cell lines (SGC-7901) and colorectal adenocarcinoma (HT-29) cells. One of the most recent studies reports the effect of some flavonoids on the central nervous system.

Halogenated flavanones and flavones are considered potential benzodiazepine receptor ligands. Indeed, 6-bromoflavone and 6-bromo-3'-nitroflavone showed activities close or higher than that of diazepam [P. Bovichelli et al, Tetrahedron Letters, 43, 5563 (2002)].

It is an object of the present invention to provide novel chalcones and flavones substituted with electronegative groups useful for the treatment of mammals (man or animal), in particular, mammals afflicted with viral and retroviral, in particular, HIV infections and methods for their synthesis.

SUMMARY

The above and other objects are realized by the present invention, one embodiment of which relates to novel compounds having the structure:

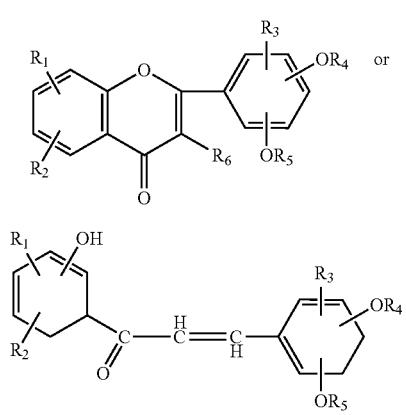

wherein:
$R_1$ is an electronegative substituent,
$R_2$ is $R_1$ or alkyl,
$R_3$ is H or O-alkyl,
$R_4$ and $R_5$ are the same or different and are alkyl, and
$R_6$ is H or OH.

A further embodiment of the invention concerns methods for the syntheses of the above described compounds comprising synthesizing the chalcones by the Claisen condensation of appropriately substituted acetophenones and benzaldehydes, preferably in ethanol and synthesizing the flavones by a three step Baker-Venkataraman rearrangement.

An additional embodiment are pharmaceutical compositions comprising therapeutically effective amounts for the treatment of viral and retroviral, in particular, HIV infections of a compound or mixture of compounds as described above and pharmaceutically acceptable carriers or excipients thereof.

A further embodiment of the invention comprises methods for the treatment of viral and retroviral, in particular, HIV infections in mammals in need thereof comprising administering thereto a therapeutically effective amount of a compound or mixture of compounds as described above.

Still further embodiments of the invention relate to (1) articles comprising packaging material which contains at least one biologically active agent contained within the packaging material, wherein the at least one therapeutic agent is effective for the treatment of a subject requiring treatment for viral and retroviral, in particular, HIV infections, and wherein the packaging material comprises a label which indicates that the therapeutic agent can be used for at least ameliorating the symptoms with which the subject is afflicted, and wherein the at least one biologically active agent is a compound or mixture of compounds as described above and (2) kits comprising, in separate packages: (A) a therapeutically effective amount of a compound or mixture of compounds as described above and (B) a carrier or excipient therefore or a biologically active agent different from the compound or mixture of compounds.

BRIEF DESCRIPTION OF THE DRAWINGS

FIGS. 1-4 are graphical depictions of the pharmacological properties of the compounds of the invention.

FIG. 1 is a graph illustrating drug inhibition on MCF-7 cells by CHBr 2M, CHCl 2M, CHNM 2M, and AZT.

FIG. 2 is a graph illustrating drug inhibition on H-9 cells by CHBr 2M, CHCl 2M, CHNM 2M, and AZT.

FIG. 3 is a graph illustrating drug inhibition on PC-3 cells by CHBr 2M, CHCl 2M, CHNM 2M, and AZT.

FIGS. 4A and 4B illustrates the structures, compositions and codes for selected chalcones (FIG. 4A) and flavones (FIG. 4B).

DETAILED DESCRIPTION

Figure 1:
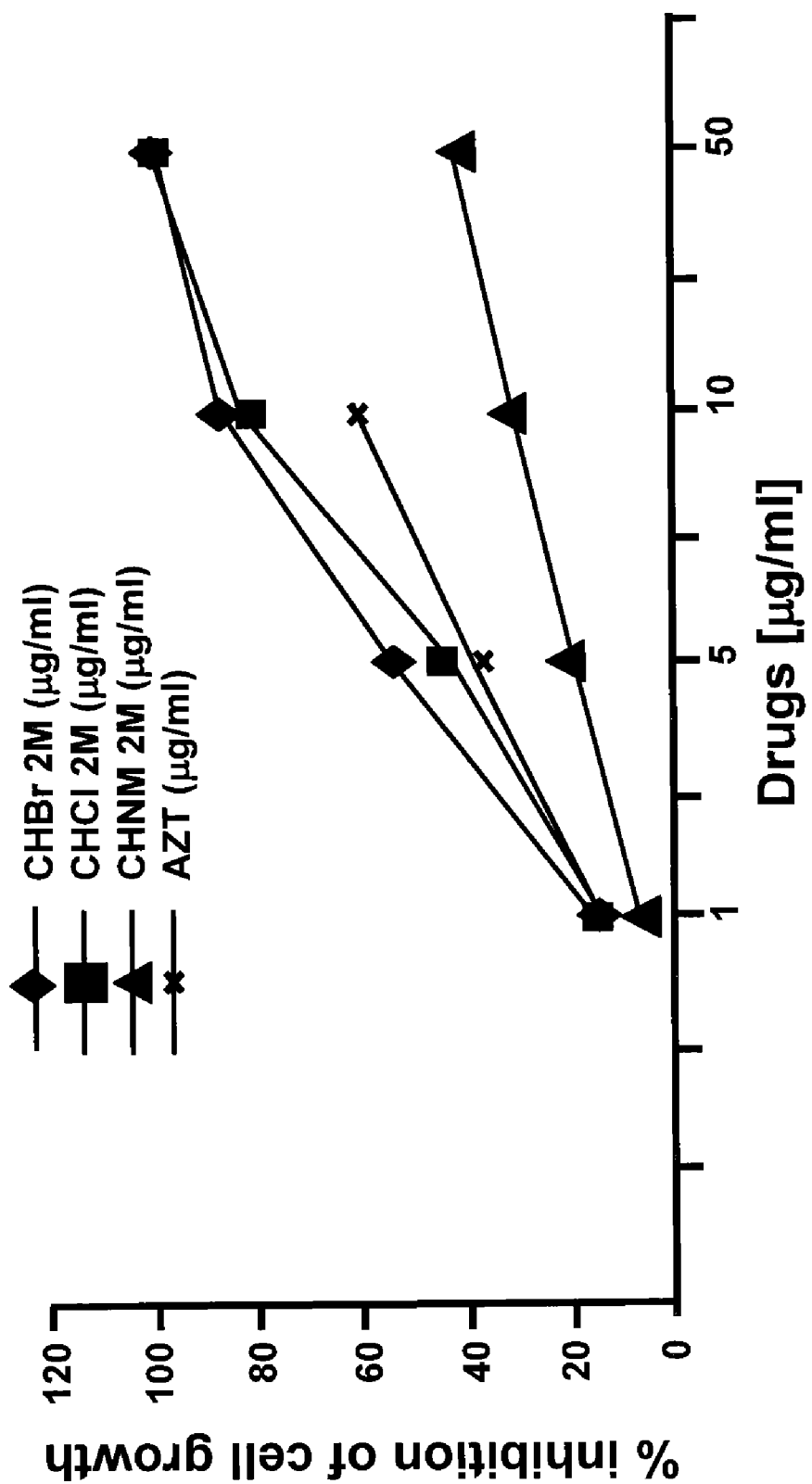

The present invention is predicated on the discovery that chalcones and flavones substituted as shown above have unexpected and unobvious therapeutic activities, in particular, anti-viral and -retroviral, in particular, anti-HIV activities.

The chalcone derivatives (5-10 in scheme 3 below and Table 1) were synthesized by Claisen condensation of appropriately substituted acetophenones and benzaldehydes, preferably in ethanol in the presence of 50% aqueous KOH. The reaction times as well as the yields vary depending upon the corresponding reagents. The compounds containing the dimethoxybenzaldehyde unit were obtained with lower yields than the trimethoxy derivatives. The crude products were contaminated with some starting materials which could easily be removed by column chromatography on silica gel using $CH_2Cl_2$:hexane as an eluent (Scheme

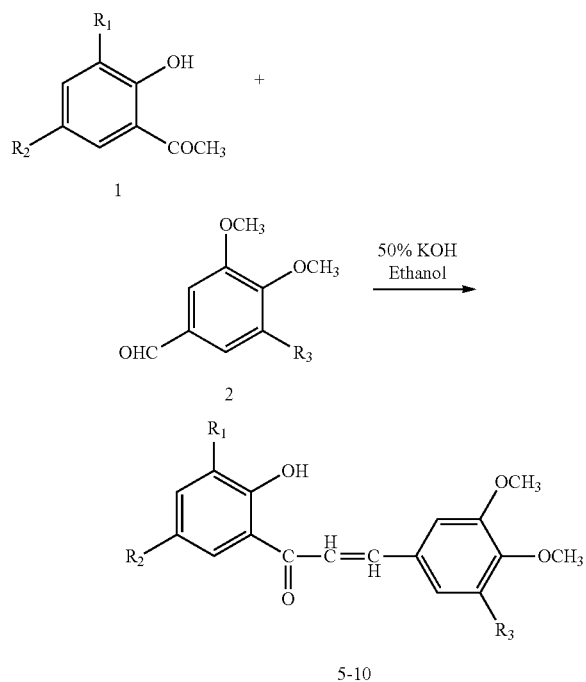

Flavones (17-22; Table 1) were synthesized using a three step Baker-Venkataraman rearrangement. The crude product was purified by recrystallization and Chromatotron chromatography using $CH_2Cl_2$:MeOH as an eluent (Scheme 4).

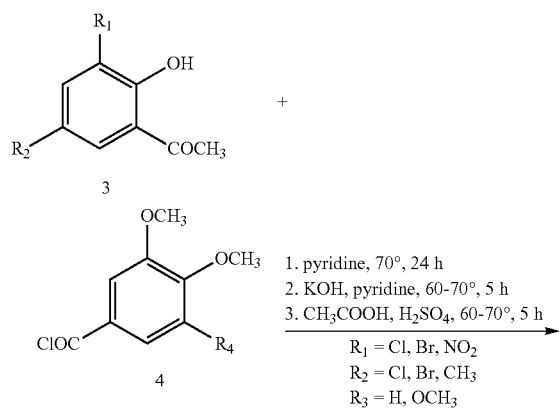

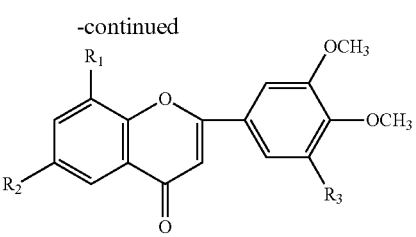

17-22

The structures of the synthesized compounds were confirmed by $^1$H-NMR, IR and elemental analysis (table 2). The compounds were subjected to tests that confirmed their cyclooxygenase-1 and cyclooxygenase-2 binding and anti-HIV activities.

In the structural formulas I and II above, the alkyl groups may be straight or branch-chain and may contain from 1 to 6 carbon atoms. Preferred alkyl groups for $R_2$, $R_3$, $R_4$ and $R_5$ are methyl, ethyl, propyl, isopropyl and tertiary butyl; most preferred being methyl.

The electronegative substituents on the molecules depicted in formulas I and II may be halogen, preferably chloro and bromo, and nitro.

As used herein, "treating" describes the management and care of a patient (human or animal) for the purpose of combating a disease, condition, or disorder and includes the administration of a compound of the present invention to prevent the onset of the symptoms or complications, alleviating the symptoms or complications, or eliminating the disease, condition or disorder.

The dosage of compound employed will depend in each case upon the nature of the cancer being treated; on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Generally, it is preferred to utilize orally administered compositions such as tablets or capsules containing 50-100 mg, administered twice a day for an adult patient weighing 70 kg (154 lbs). It will be understood by those skilled in the art, however, that any suitable mode of administration and appropriate dosage may be employed in the practice of the invention.

Although the methods and compositions of the invention may be employed to treat any viral and retroviral infection sensitive to the compounds of the invention, the invention is particularly suited for the treatment of HIV infections.

In the examples below, melting points were determined on a Gallenkamp Melting Point Apparatus and were uncorrected. Infrared spectra were obtained on a Perkin Elmer FTIR 1430 spectrophotometer, using KBr pellets. $^1$H-NMR and $^{13}$C-NMR spectra were obtained with a Brucker HX-300 spectrometer and the chemical shifts were reported as parts per million (δ ppm) downfield.

Column chromatography as well as Chromatotron 8924 (Harrison Research) instruments were used for purification of the compounds. Davisil Chromatographic Silica gel (200-425 mesh) was used for column chromatographic separations and Silica gel Merck, TLC grade 7749 with gypsum binder and fluorescent indicator was used for the preparation of the Chromatotron rotors. All reactions and purification procedures were monitored using Whatman TLC plates with a fluorescent indicator.

As noted above and shown in Scheme 5, chalcone derivatives are synthesized by the Claisen condensation of appropriately substituted and commercially available acetophenones and benzaldehydes in ethanol in the presence of 50% aqueous KOH. Corresponding substituted acetophenones were mixed with an equimolar amount of substituted benzaldehydes in ethanol. 5 milliliters of 50% aqueous KOH was added and the reaction mixture heated at 50-60° C. for 2-6 h. The product precipitated after cooling as yellow crystals, which were collected, recrystallized from CH₃OH/CH₂Cl and finally purified by column chromatography, using CH₂Cl₂:hexane 5:1 as eluent.

Synthesis of substituted chalcones: the methylated chalcone was synthesized by selective dealkylation of commercially available 2,4,6-trihydroxybenzaldehyde in the presence of aluminum tribromide using acetonitrile as the solvent. The aldehyde was reduced by means of triethylsilane in trifluoroacetic acid. Acylation of the product with acetic anhydride gave the appropriately substituted precursor for chalcone formation.

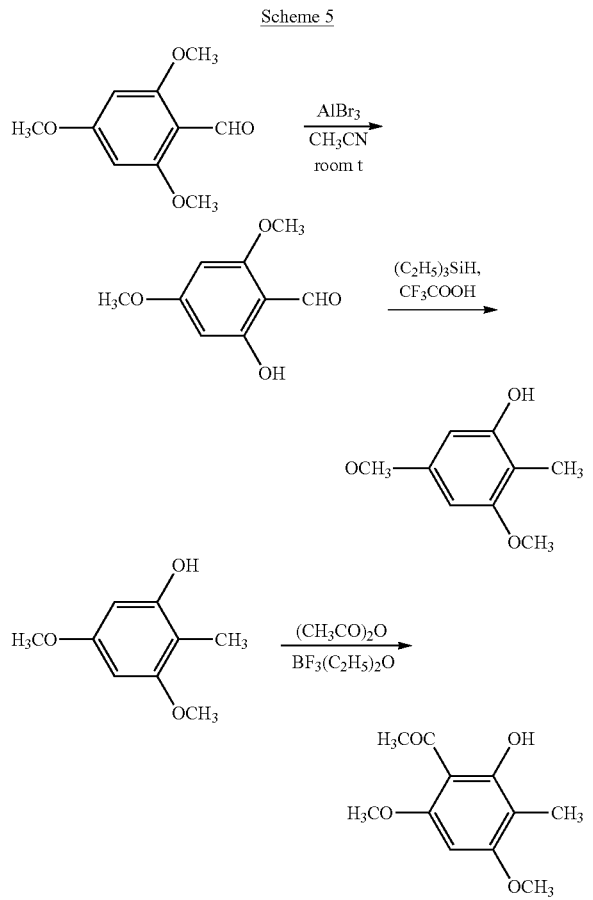

Scheme 5

Synthesis of methyl acetophenone

Methyl substituted

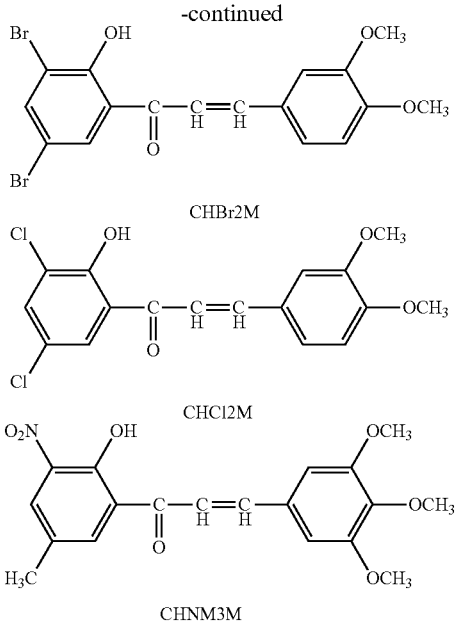

CHBr2M

CHCl2M

CHNM3M

EXAMPLE 1

Synthesis of Chalcones 5-10

Employing the general method described by N. N. Mateeva et al, J. Heterocyclic Chem., 39, 1251 (2002); D. K. Bhardwaj et al, Indian J. Chem., 27B, 261 (1988) and K. Krohn et al, Phytochemistry 6 1.93 1 (2002), the corresponding substituted acetophenones 1 were mixed with an equimolar amount of 3,4-dimethoxybenzaldehyde or 3,4,5-trimethoxybenzaldehyde, 2, in ethanol (Scheme 3). 5 Milliliters of 50% aqueous KOH was added and the reaction mixture heated at 50-60° C. for 2-6 h. The product precipitated after cooling as yellow crystals, which were collected, recrystallized from CH₃OH/CH₂Cl₂ and finally purified by column chromatography, using CH₂Cl₂:hexane 5:1 as eluent. The yields were 60-80%.

EXAMPLE 2

Synthesis of Flavones 17-22

Employing the general method described by Mateeva, supra, T. Hone et al, Chem. Pharm. Bull., 43,2054 (1995) and C. J. Bennett et al, Bioorganic & Medicinal Chemistry, 12, 2079 (2004). Compounds 3 (Scheme 4) were mixed with 1.7 times excess of 3,4,5-trimethoxy benzoyl chloride or 3,4-dimethoxy benzoyl chloride, 4, correspondingly, in pyridine. The reaction mixture was heated at 70° C. for 4 h, and then poured onto ice containing 5 N HCL. The precipitate that formed was collected by vacuum filtration and air dried. The crude product was dissolved in pyridine in the presence of 10 times excess of KOH.

The reaction was carried out for 4 h at 65° C., and then the mixture poured onto an iced 5N HCl bath. A yellow precipitate was formed, which was collected by filtration and air dried. The crude product was dissolved in acetic acid containing 1 mL concentrated H₂SO₄, heated at 60° C. for 4 h and left stirring overnight at room temperature. After 24 h, the reaction mixture was poured onto an ice-NaHCO₃ mixture, the product collected by filtration and recrystallized from ethanol.

The pure flavone was obtained by purification on Chromatotrone with $CH_2Cl_2$:MeOH 8:1 as eluent. The yields were 30-50%.

The purified and identified analogs were subjected to in vitro biological testing. The results of the testing clearly demonstrated inhibition of the H-9 cell lines (the HIV or cancer virus cell lines), as well as significant inhibition of the MCF-7 cell lines (breast cancer cells) and PC-3 cell lines (prostate cancer cell lines). See tables 3-17. The biological activities of the flavonoids were compared with the activity of AZT (a well established anti-HIV and anti-cancer drug) under the same conditions. Three compounds (CHBr2M, CHCl2M and CHNM3M) showed a much superior inhibitory activities, compared to AZT when assayed against the above mentioned cell lines under the same conditions.

TABLE 1

Elemental Analysis and Melting Point Data for the Synthesized Compounds

| Compound | | Composition | Elemental Analysis Calculated/Found | m.p. °C. |
|---|---|---|---|---|
| 5 | $R_1=R_2=Cl, R_3=OCH_3$ | $C_{18}H_{16}Cl_2O_5$ | C56.41 H4.21<br>C56.31 H4.41 | 145-146 |
| 6 | $R_1=R_2=Br, R_3=OCH_3$ | $C_{18}H_{16}Br_2O_5$ | C45.79 H3.42<br>C56.41 H4.21 | 152-153 |
| 7 | $R_1=NO_2, R_2=CH_3, R_3=OCH_3$ | $C_{19}H_{19}NO_7$ | C61.12 H5.13<br>C61.11 H5.40 | 147-148 |
| 8 | $R_1=R_2=Cl, R_3=H$ | $C_{17}H_{14}Cl_2O_4$ | C57.81 H4.00<br>C58.03 H4.39 | 163-164 |
| 9 | $R_1=R_2=Br, R_3=H$ | $C_{17}H_{14}Br_2O_4$ | C46.18 H3.19<br>C46.29 H3.43 | 158-159 |
| 10 | $R_1=NO_2, R_2=CH_3, R_3=H$ | $C_{18}H_{17}NO_6$ | C62.97 H4.99<br>C62.97 H5.33 | 153-154 |
| 11 | $R_1=R_2=Cl, R_3=OCH_3$ | $C_{18}H_{14}Cl_2O_6$ | C54.43 H3.55<br>C54.36 H3.85 | 198-199 |
| 12 | $R_1=R_2=Br, R_3=OCH_3$ | $C_{18}H_{16}Br_2O_6$ | C44.47 H2.90<br>C44.12 H3.19 | >260, decomp |
| 13 | $R_1=NO_2, R_2=CH_3, R_3=OCH_3$ | $C_{19}H_{17}NO_8$ | C58.92 H4.42<br>C58.97 H4.71 | 210-211 |
| 14 | $R_1=R_2=Cl, R_3=H$ | $C_{17}H_{12}Cl_2O_5$ | C55.61 H3.29<br>C55.41 H3.45 | 215-216 |
| 15 | $R_1=R_2=Br, R_3=H$ | $C_{17}H_{12}Br_2O_5$ | C44.77 H2.65<br>C44.81 H2.99 | 220-221 |
| 16 | $R_1=NO_2, R_2=CH_3, R_3=H$ | $C_{18}H_{15}NO_7$ | C60.50 H4.23<br>C60.41 H4.21 | 195-196 |
| 17 | $R_1=R_2=Cl, R_3=OCH_3$ | $C_{18}H_{14}Cl_2O_5$ | C56.71 H3.70<br>C57.03 H3.81 | 155-156 |
| 18 | $R_1=R_2=Br, R_3=OCH_3$ | $C_{18}H_{14}Br_2O_5$ | C45.99 H3.00<br>C46.28 H3.39 | 179-180 |
| 19 | $R_1=NO_2, R_2=CH_3, R_3=OCH_3$ | $C_{19}H_{17}NO_7$ | C61.45 H4.61<br>C561.47 H5.01 | 135-136 |
| 20 | $R_1=R_2=Cl, R_3=H$ | $C_{17}H_{12}Cl_2O_4$ | C58.14 H3.44<br>C58.37 H3.76 | 145-146 |
| 21 | $R_1=R_2=Br, R_3=H$ | $C_{17}H_{12}Br_2O_4$ | C46.40 H2.75<br>C46.72 H3.12 | 134-135 |
| 22 | $R_1=NO_2, R_2=CH_3, R_3=H$ | $C_{18}H_{15}NO_6$ | C63.34 H4.43<br>C62.95 H4.80 | 150-151 |

TABLE 2

NMR and IR Data for the Synthesized Compounds

| Compound | 1H-NMR (δ ppm) | IR (ν cm$^{-1}$ KBr) |
|---|---|---|
| 5 | (DMSO-$d_6$): δ 3.70, 3.79 (s, s, 9H, —$CH_3O$), 6.82 (s, 2H, Ar), 7.07-7.08 (d, 1H, Ar, J = 3.0 Hz), 7.42-7.43 (d, 1H, Ar, J = 3.0 Hz), 7.37-7.42 (d, 1H, CH=CH, J = 15 Hz), 8.55-8.60 (d, 1H, CH=CH, J = 15 Hz) | 3400 (broad, OH)<br>1590 (C=O),<br>1610 (C=C Ar),<br>1590 (C=C),<br>1130 (C—O) cm$^{-1}$ |
| 6 | (DMSO-$d_6$): δ 3.78, 3.80 (s, s, 9H, —$CH_3O$), 7.14 (s, 2H, Ar), 7.34-7.35 (d, 1H, Ar, J = 3.0 Hz), 7.39-7.45 (d, 1H, Ar, J = 18 Hz, CH=CH, J = 15 Hz) 7.58-7.59 (d, 1H, Ar, J = 3.0 Hz), 8.48-8.53 (d, 1H, J = 18 Hz) | 3390 (broad, OH)<br>1585 (C=O),<br>1600 (C=C Ar),<br>1595 (C=C),<br>1110 (C—O) cm$^{-1}$ |
| 7 | (DMSO-$d_6$): δ 3.81, 3.84 (s, s, 9H, —$CH_3O$), 6.87 (s, 2H, Ar), 7.37-7.43 (d, 1H, Ar, J = 18 Hz CH=CH), 7.48-7.49 (d, 1H, J = 3.0 Hz, Ar), 8.08-8.14 (d, 1H, J = 18 Hz, CH=CH) | 3390 (broad, OH)<br>1640 (C=O),<br>1612 (C=C Ar),<br>1580 (C=C),<br>1120 (C—O) cm$^{-1}$ |
| 8 | (DMSO-$d_6$): δ 3.93, 3.97 (s, s, 6H, —$CH_3O$), 6.88-6.92 (m, 1H, Ar), 7.15-7.16 (d, 1H, J = 3.0 Hz, Ar), 7.24-7.29 (m, 1H, Ar), 7.34-7.39 (d, 1H, J = 15 Hz, CH=CH), 7.54-7.57 (m, 1H, Ar), 7.80-7.81 (d, 1H, J = 3.0 Hz, Ar), 7.91-7.96 (d, 1H, J = 15 Hz, CH=CH) | 3400 (broad, OH)<br>1650 (C=O),<br>1610 (C=C Ar),<br>1590 (C=C),<br>1125 (C—O) cm$^{-1}$ |

TABLE 2-continued

NMR and IR Data for the Synthesized Compounds

| Compound | 1H-NMR (δ ppm) | IR (ν cm$^{-1}$ KBr) |
|---|---|---|
| 9 | (DMSO-d$_6$): δ 3.07, 3.10 (s, s, 6H, —CH$_3$O), 6.88-6.92 (m, 1H, Ar), 7.15-7.16 (d, 1H, Ar), 7.26-7.30 (dd, 1H, Ar), 7.34-7.39 (d, 1H, J = 15 Hz, CH=CH), 7.86-7.91 (d, 1H, J = 15 Hz, CH=CH), 7.94-7.98 (m, 1H, Ar) | 3390 (broad, OH) 1650 (C=O), 1611 (C=C Ar), 1590 (C=C), 1110 (C—O) cm$^{-1}$ |
| 10 | (DMSO-d$_6$): δ 3.77, 3.80 (s, s, 6H, —CH$_3$O), 6.95-6.98 (d, 1H, J = 9 H), 7.17 (s, 1H, Ar), 7.22-7.23 (d, 1H, J = 3.0 Hz, Ar), 7.40-7.45 (d, 1H, J = 15 Hz, CH=CH), 7.65-7.66 (d, 1H, J = 3.0 Hz, Ar), 798-8.03 (d, 1H, J = 15 Hz, CH=CH) | 3390 (broad, OH) 1640 (C=O), 1610 (C=C Ar), 1592 (C=C), 1120 (C—O) cm$^{-1}$ |
| 11 | (DMSO-d$_6$): δ 3.68, 3.81 (s, s, 9H, —CH$_3$O), 7.83-7.84 (d, 1H, Ar, J = 2.4 Hz), 7.85-7.86 (d, 1H, Ar, J = 2.4 Hz), 8.08 (s, 2H, Ar) | 3400 (broad, OH) 1650 (C=O), 1613 (C=C Ar), 1590 (C=C), 1131 (C—O) cm$^{-1}$ |
| 12 | (DMSO-d$_6$): δ 3.68, 3.81 (s, s, 9H, —CH$_3$O), 7.98-7.99 (d, 1H, Ar, J = 2.4 Hz), 8.01-8.02 (d, 1H, Ar, J = 2.4 Hz), 8.19 (s, 2H, Ar) | 3390 (broad, OH) 1655 (C=O), 1605 (C=C Ar), 1580 (C=C), 1115 (C—O) cm$^{-1}$ |
| 13 | (DMSO-d$_6$): δ 3.76, 3.86 (s, s, 6H, —CH$_3$O), 7.69 (s, 2H, Ar), 8.25-8.26 (d, 1H, J = 3.0 Hz, Ar), 8.42-8.43 (d, 1H, J = 3.0 Hz, Ar). | 3410 (broad, OH) 1660 (C=O), 1613 (C=C Ar), 1595 (C=C), 1115 (C—O) cm$^{-1}$ |
| 14 | (DMSO-d$_6$): δ 3.79 (s, s, 9H, —CH$_3$O), 7.01-7.04 (d, 1H, Ar, J = 9.0 Hz), 7.81 (s, 1H, Ar), 7.87 (m, 1H, Ar), 8.12-8.15 (d, 1H, Ar, J = 9.0 Hz), 8.44 (s, 1H, Ar) | 3380 (broad, OH) 1645 (C=O), 1610 (C=C Ar), 1595 (C=C), 1120 (C—O) cm$^{-1}$ |
| 15 | (DMSO-d$_6$): δ 3.29, 3.31 (s, s, 6H, —CH$_3$O), 7.17-7.19 (d, 1H, Ar, J = 6 Hz), 7.88-7.98 (m, 2H, Ar,), 8.14-8.15 (d, 1H, J = 3.0 Hz), 8.34-8.35 (d, 1H, Ar, J = 3.0 Hz) | 3400 (broad, OH) 1656 (C=O), 1600 (C=C Ar), 1595 (C=C), 1130 (C—O) cm$^{-1}$ |
| 16 | (DMSO-d$_6$): δ 3.77, 3.80 (s, s, 6H, —CH$_3$O), 6.97-6.99 (m, 2H, Ar), 8.16 (s, 1H, Ar), 8.33-8.35 (dd, J = 6 Hz, Ar), 8.48 (s, 1H, Ar) | 3380 (broad, OH) 1660 (C=O), 1610 (C=C Ar), 1588 (C=C), 1130 (C—O) cm$^{-1}$ |
| 17 | (deuteriochloroform): δ 3.87, 3.89 (s, 9H, —CH$_3$O), 8.01-8.02 (d, J = 2.4 Hz, 1H, Ar), 7.67-7.68 (d, J = 2.4 Hz, 1H, Ar), 6.74 (s, 1H, O=C—CH=), 7.14 (s, 2H, Ar) | 1660 (C=O), 1613 (C=C Ar), 1592 (C=C), 1133 (C—O) cm$^{-1}$ |
| 18 | (deuteriochloroform): δ 3.93, 3.94 (s, 9H, —CH$_3$O), 8.27-8.28 (d, J = 2.2 Hz, 1H, Ar), 8.02-8.03 (d, J = 2.2 Hz, 1H, Ar), 6.80 (s, 1H, O=C—CH=), 7.23 (s, 2H, Ar) | 1656 (C=O), 1610 (C=C Ar), 1591 (C=C), 1134 (C—O) cm$^{-1}$ |
| 19 | (deuteriochloroform): δ 3.87, 3.91 (s, 9H, —CH$_3$O), 8.24 (s, 1H, Ar), 8.19-8.20 (d, J = 2.1 Hz, 1H, Ar), 6.79 (s, 1H, O=C—CH=), 7.23 (s, 2H, Ar), 2.49 (s, 3H, —CH$_3$) | 1654 (C=O), 1618 (C=C Ar), 1583 (C=C), 1126 (C—O) cm$^{-1}$ |
| 20 | (deuteriochloroform): δ 3.95, 3.96 (s, 6H, —CH$_3$O), 8.07-8.06 (d, J = 2.3 Hz, 1H, Ar), 7.70-7.71 (d, J = 2.6 Hz, 1H, Ar), 6.77 (s, 1H, O=C—CH=), 6.67-6.99 (d, J = 8.4 Hz, 1H, Ar) 7.44-7.45 (d, J = 2.0 Hz, 1H, Ar), (td, J = 2.3, 8.7 Hz, 1H, Ar) | 1654 (C=O), 1561 (C=C Ar), 1519 (C=C), 1278 (C—O) cm$^{-1}$ |
| 21 | (deuteriochloroform): δ 3.92, 3.93 (s, 6H, —CH$_3$O), 8.26-8.27 (d, J = 2.4 Hz, 1H, Ar), 7.99-8.0 (d, J = 2.2 Hz, 1H, Ar), 6.82 (s, 1H, O=C—CH=), 6.67-6.99 (d, J = 8.4 Hz, 1H, Ar), 7.74-7.77 (dd, J = 1.9 Hz, 6.4 Hz 1H, Ar), 7.57-7.58 (d, J = 1.6 Hz, 6.4 Hz 1H, Ar), 6.88-6.91 (d, J = 8.5 Hz 1H, Ar) | 1677 (C=O), 1650 (C=C Ar), 1599 (C=C), 1235 (C—O) cm$^{-1}$ |
| 22 | (deuteriochloroform): δ 3.96, 4.00 (s, 6H, —CH$_3$O), 8.30 (s, 1H, Ar), 8.22-8.23 (d, J = 2.0 Hz, 1H, Ar), 6.84 (s, 1H, O=C—CH=), 6.97-7.00 (d, J = 8.9 Hz, 1H, Ar), 7.82-8.00 (dd, J = 1.8 Hz, 50.3, 1H, Ar), 7.58-7.59 (d, J = 2.0 Hz, 1H, Ar), 2.54 (s, 3H, —CH$_3$) | 1647 (C=O), 1615 (C=C Ar), 1531 (C=C), 1256 (C—O) cm$^{-1}$ |

TABLE 3

K. K. Redda/Chavor Exp.: H-9 Cells — Cytoxicity on H-9 cells — Dec. 05 to Dec. 09, 2005

| Drugs | Cells (×10⁴) | Mean | SD | % Inhibition | Mean | SD |
|---|---|---|---|---|---|---|
| 2% DMSO | 49.5 | | | | | |
|  | 50.5 | 50.25 | 0.54 | 0 | | |
|  | 50.8 | | | | | |
| AZT (μg/ml) | 41.3 | | | 17.91 | | |
| 1 | 37.5 | 40.83 | 2.57 | 25.37 | 18.74 | 5.11 |
|  | 43.8 | | | 12.94 | | |
| 5 | 30.5 | | | 39.30 | | |
|  | 30.0 | 30.92 | 0.96 | 40.30 | 38.47 | 1.92 |
|  | 32.3 | | | 35.82 | | |
| 10 | 26.0 | | | 48.26 | | |
|  | 25.0 | 25.25 | 0.54 | 50.25 | 49.75 | 1.07 |
|  | 24.8 | | | 50.75 | | |
| CHBr 2M (μg/ml) | 45.5 | | | 9.45 | | |
| 1 | 49.5 | 47.42 | 1.64 | 1.49 | 5.64 | 3.26 |
|  | 47.3 | | | 5.97 | | |
| 5 | 25.5 | | | 49.25 | | |
|  | 24.8 | 25.33 | 0.42 | 50.76 | 49.59 | 0.85 |
|  | 25.8 | | | 48.76 | | |
| 10 | 18.3 | | | 63.68 | | |
|  | 16.3 | 17.58 | 0.94 | 67.66 | 65.01 | 1.88 |
|  | 18.3 | | | 63.88 | | |
| 50 | 11.8 | | | 76.62 | | |
|  | 11.5 | 11.58 | 0.12 | 77.11 | 76.95 | 0.23 |
|  | 11.5 | | | 77.11 | | |
| CHCl 2M (μg/ml) | 42.0 | | | 16.42 | | |
| 1 | 42.3 | 42.25 | 0.20 | 15.92 | 15.92 | 0.41 |
|  | 42.6 | | | 15.42 | | |
| 5 | 24.0 | | | 52.24 | | |
|  | 23.8 | 24.00 | 0.20 | 52.74 | 52.24 | 0.41 |
|  | 24.3 | | | 51.74 | | |
| 10 | 13.0 | | | 74.13 | | |
|  | 11.5 | 12.92 | 1.12 | 77.11 | 74.30 | 2.24 |
|  | 14.3 | | | 71.64 | | |
| 50 | 4.0 | | | 92.04 | | |
|  | 4.5 | 4.50 | 0.41 | 91.04 | 91.04 | 0.81 |
|  | 5.0 | | | 90.05 | | |
| CHNM 2M (μg/ml) | 57.3 | | | −13.93 | | |
| 1 | 60.3 | 58.17 | 1.48 | −19.90 | −15.75 | 2.94 |
|  | 57.0 | | | −13.43 | | |
| 5 | 61.5 | | | −22.39 | | |
|  | 55.5 | 58.58 | 2.45 | −10.45 | −16.58 | 4.88 |
|  | 58.8 | | | −16.92 | | |
| 10 | 50.5 | | | −0.50 | | |
|  | 52.3 | 50.75 | 1.14 | −3.98 | −1.00 | 2.26 |
|  | 49.5 | | | 1.49 | | |
| 50 | 56.8 | | | −12.94 | | |
|  | 54.8 | 56.00 | 0.89 | −8.96 | −11.44 | 1.77 |
|  | 56.5 | | | −12.44 | | |
| H-9 Mean | | | | | | |

TABLE 4

| | 1 | 5 | 10 | 50 |
|---|---|---|---|---|
| Drugs (μg/ml) | | | | |
| CHBr 2M (μg/ml) | 5.64 | 49.59 | 65.01 | 76.95 |
| CHCl 2M (μg/ml) | 15.92 | 52.24 | 74.3 | 91.04 |
| CHNM 2M (μg/ml) | −15.75 | −16.58 | −1 | −11.44 |
| AZT (μg/ml) | 18.74 | 38.47 | 49.75 | |
| SD Drugs | | | | |
| CHBr 2M (μg/ml) | 3.26 | 0.85 | 1.88 | 0.23 |
| CHCl 2M (μg/ml) | 0.41 | 0.41 | 2.24 | 0.81 |
| CHNM 2M (μg/ml) | 2.94 | 4.88 | 2.26 | 1.77 |
| AZT (μg/ml) | 5.11 | 1.82 | 1.07 | |

TABLE 5

K. K. Redda/Chavor Exp.: MCF-7 cells — Cytoxicity on MCF-7 cells — Nov. 14 to Nov. 18, 2005

| Drugs | Cells (×10⁴) | Mean | SD | % Inhibition | Mean | SD |
|---|---|---|---|---|---|---|
| 2% DMSO | 56.8 | | | | | |
|  | 61.8 | 57.83 | 2.86 | 0 | | |
|  | 65.0 | | | | | |
| AZT (μg/ml) | 53.0 | | | 8.36 | | |
| 1 | 55.3 | 53.83 | 1.01 | 4.47 | 6.92 | 1.74 |
|  | 53.3 | | | 7.93 | | |
| 5 | 34.8 | | | 39.91 | | |
|  | 34.5 | 35.50 | 1.24 | 40.35 | 38.62 | 2.15 |
|  | 37.3 | | | 35.59 | | |
| 10 | 22.3 | | | 61.53 | | |
|  | 23.0 | 22.50 | 0.35 | 60.23 | 61.10 | 0.61 |
|  | 22.3 | | | 61.53 | | |
| CHBr 2M (μg/ml) | 48.6 | | | 15.71 | | |
| 1 | 51.5 | 49.08 | 1.85 | 10.95 | 15.13 | 3.20 |
|  | 47.0 | | | 18.73 | | |
| 5 | 27.0 | | | 53.31 | | |
|  | 25.3 | 26.25 | 0.74 | 56.34 | 54.61 | 1.27 |
|  | 26.5 | | | 54.18 | | |
| 10 | 7.3 | | | 87.46 | | |
|  | 9.0 | 7.92 | 0.77 | 84.44 | 86.31 | 1.34 |
|  | 7.5 | | | 87.03 | | |
| 50 | 0.8 | | | 98.70 | | |
|  | 1.0 | 0.75 | 0.20 | 98.27 | 98.70 | 0.35 |
|  | 0.5 | | | 99.14 | | |
| CHCl 2M (μg/ml) | 49.8 | | | 13.98 | | |
| 1 | 48.5 | 49.42 | 0.66 | 16.14 | 14.55 | 1.13 |
|  | 50.0 | | | 13.54 | | |
| 5 | 32.0 | | | 44.67 | | |
|  | 31.5 | 32.33 | 0.85 | 45.53 | 44.09 | 1.47 |
|  | 33.5 | | | 42.07 | | |
| 10 | 10.0 | | | 82.71 | | |
|  | 10.8 | 10.42 | 0.31 | 81.41 | 81.99 | 0.54 |
|  | 10.5 | | | 81.84 | | |
| 50 | 1.0 | | | 98.27 | | |
|  | 0.5 | 0.75 | 0.20 | 99.14 | 98.70 | 0.35 |
|  | 0.8 | | | 98.70 | | |
| CHNM 2M (μg/ml) | 53.0 | | | 8.36 | | |
| 1 | 55.3 | 53.92 | 0.96 | 4.47 | 6.77 | 1.67 |
|  | 53.5 | | | 7.49 | | |
| 5 | 45.5 | | | 21.33 | | |
|  | 45.0 | 46.17 | 1.31 | 22.19 | 20.17 | 2.27 |
|  | 48.0 | | | 17.00 | | |
| 10 | 40.5 | | | 29.97 | | |
|  | 39.0 | 39.75 | 0.61 | 32.56 | 31.27 | 1.06 |
|  | 39.8 | | | 31.27 | | |
| 50 | 32.5 | | | 43.80 | | |
|  | 34.5 | 33.50 | 0.82 | 40.35 | 42.07 | 1.41 |
|  | 33.5 | | | 42.07 | | |
| MCF-7 Mean | | | | | | |

TABLE 6

K. K. Redda/Chavor Exp.: PC-3 Cells — Cytoxicity on PC-3 cells — Nov. 11 to Nov. 17, 2005

| Drugs | Cells (×10⁴) | Mean | SD | % Inhibition | Mean | SD |
|---|---|---|---|---|---|---|
| 2% DMSO | 99.3 | | | | | |
|  | 98.3 | 98.00 | 1.14 | 0 | | |
|  | 96.5 | | | | | |
| AZT (µg/ml) | 84.0 | | | 14.29 | | |
| 1 | 85.5 | 84.58 | 0.66 | 12.76 | 13.69 | 0.67 |
|  | 84.3 | | | 14.03 | | |
| 5 | 70.5 | | | 28.06 | | |
|  | 72.3 | 17.33 | 0.72 | 26.28 | 27.21 | 0.73 |
|  | 71.3 | | | 27.30 | | |
| 10 | 61.5 | | | 37.24 | | |
|  | 61.3 | 61.58 | 0.31 | 37.50 | 37.16 | 0.32 |
|  | 62.0 | | | 36.73 | | |
| CHBr 2M (µg/ml) | 73.3 | | | 25.26 | | |
| 1 | 72.0 | 70.92 | 2.47 | 26.53 | 27.64 | 2.52 |
|  | 67.5 | | | 31.12 | | |
| 5 | 75.5 | | | 22.96 | | |
|  | 68.0 | 70.83 | 3.32 | 30.61 | 27.72 | 3.39 |
|  | 69.0 | | | 29.50 | | |
| 10 | 77.5 | | | 20.92 | | |
|  | 70.0 | 72.25 | 3.72 | 28.57 | 26.28 | 3.80 |
|  | 69.3 | | | 29.34 | | |
| 50 | 57.5 | | | 41.33 | | |
|  | 53.0 | 56.00 | 2.12 | 45.92 | 42.86 | 2.16 |
|  | 57.5 | | | 41.33 | | |
| CHCl 2M (µg/ml) | 74.3 | | | 24.23 | | |
| 1 | 74.0 | 73.42 | 1.01 | 24.49 | 25.09 | 1.03 |
|  | 72.0 | | | 26.53 | | |
| 5 | 69.0 | | | 29.59 | | |
|  | 69.5 | 70.00 | 1.08 | 29.08 | 28.57 | 1.10 |
|  | 71.5 | | | 27.04 | | |
| 10 | 68.0 | | | 30.61 | | |
|  | 70.0 | 69.58 | 1.16 | 28.57 | 29.00 | 1.18 |
|  | 70.8 | | | 27.81 | | |
| 50 | 67.3 | | | 31.88 | | |
|  | 65.5 | 62.08 | 6.11 | 33.16 | 36.65 | 6.24 |
|  | 53.5 | | | 45.41 | | |
| CHNM 2M (µg/ml) | 88.5 | | | 9.69 | | |
| 1 | 81.3 | 89.08 | 6.65 | 17.09 | 9.10 | 6.78 |
|  | 97.5 | | | 0.51 | | |
| 5 | 59.5 | | | 39.29 | | |
|  | 61.8 | 62.67 | 3.03 | 36.99 | 36.05 | 3.09 |
|  | 66.8 | | | 31.89 | | |
| 10 | 62.5 | | | 36.22 | | |
|  | 60.3 | 62.92 | 2.37 | 38.52 | 35.80 | 2.41 |
|  | 66.0 | | | 32.65 | | |
| 50 | 49.8 | | | 49.23 | | |
|  | 52.5 | 50.17 | 1.76 | 46.43 | 48.81 | 1.80 |
|  | 48.3 | | | 50.77 | | |
| PC-3 mean | | | | | | |

TABLE 7

Drug Inhibition on PC-3 cells

|  | 1 | 5 | 10 | 50 |
|---|---|---|---|---|
| Drugs (µg/ml) | | | | |
| CHBr 2M (µg/ml) | 47.1 | 65.88 | 78.04 | 89.50 |
| CHCl 2M (µg/ml) | 42.4 | 73.76 | 87.02 | 96.96 |
| CHNM 2M (µg/ml) | 27.9 | 39.36 | 45.03 | 59.67 |
| AZT (µg/ml) | 17.27 | 43.23 | 59.67 | |
| SD Drugs | | | | |
| CHBr 2M (µg/ml) | 0.78 | 2.25 | 0.59 | 1.09 |
| CHCl 2M (µg/ml) | 2.11 | 0.85 | 0.52 | 0.20 |

TABLE 7-continued

Drug Inhibition on PC-3 cells

|  | 1 | 5 | 10 | 50 |
|---|---|---|---|---|
| CHNM 2M (µg/ml) | 0.59 | 1.37 | 0.98 | 2.18 |
| AZT (µg/ml) | 0.39 | 0.90 | 1.41 | |

TABLE 8

Drug Inhibition on MCF-7 Cells

|  | 1 | 5 | 10 | 50 |
|---|---|---|---|---|
| Drugs (µg/ml) | | | | |
| CHBr 2M (µg/ml) | 15.13 | 54.61 | 86.31 | 98.709 |
| CHCl 2M (µg/ml) | 14.55 | 44.09 | 81.99 | 98.70 |
| CHNM 2M (µg/ml) | 6.77 | 20.17 | 31.27 | 42.07 |
| AZT (µg/ml) | 6.92 | 38.62 | 61.1 | |
| SD Drugs | | | | |
| CHBr 2M (µg/ml) | 3.2 | 1.27 | 1.34 | 0.35 |
| CHCl 2M (µg/ml) | 1.13 | 1.47 | 0.54 | 0.35 |
| CHNM 2M (µg/ml) | 1.67 | 2.27 | 1.06 | 1.14 |
| AZT (µg/ml) | 1.74 | 2.15 | 0.61 | |

TABLE 9

K. K. Redda/Chavor Exp.: MCF-7 Cells — Cytoxicity on MCF-7 cells — Sep. 26 to Sep. 30, 2005

| Drugs | Cells (×10⁴) | Mean | SD | % Inhibition | Mean | SD |
|---|---|---|---|---|---|---|
| 2% DMSO | 49.0 | | | | | |
|  | 50.5 | 49.58 | 0.66 | 0 | | |
|  | 49.3 | | | | | |
| AZT (µg/ml) | 35.5 | | | 28.40 | | |
| 1 | 36.8 | 36.42 | 0.66 | 25.88 | 26.55 | 1.32 |
|  | 37.0 | | | 25.38 | | |
| 5 | 24.8 | | | 49.98 | | |
|  | 27.3 | 26.35 | 1.10 | 45.04 | 46.86 | 2.22 |
|  | 27.0 | | | 45.55 | | |
| 10 | 17.3 | | | 65.21 | | |
|  | 18.3 | 17.25 | 0.82 | 63.19 | 65.21 | 1.65 |
|  | 16.3 | | | 67.23 | | |
| CM-091303 (µg/ml) | 35.8 | | | 27.90 | | |
| 1 | 35.8 | 36.17 | 0.59 | 27.90 | 27.06 | 1.19 |
|  | 37.0 | | | 25.38 | | |
| 5 | 35.3 | | | 28.91 | | |
|  | 36.8 | 35.75 | 0.71 | 25.88 | 27.90 | 1.43 |
|  | 35.3 | | | 28.91 | | |
| 10 | 29.8 | | | 40.00 | | |
|  | 29.3 | 30.17 | 0.96 | 41.01 | 39.16 | 1.95 |
|  | 31.5 | | | 36.47 | | |
| 50 | 26.3 | | | 47.06 | | |
|  | 26.8 | 26.17 | 0.51 | 46.5 | 47.23 | 1.04 |
|  | 25.5 | | | 48.57 | | |
| CM-090803 (µg/ml) | 33.8 | | | 31.93 | | |
| 1 | 33.5 | 33.33 | 0.42 | 32.44 | 32.77 | 0.86 |
|  | 32.8 | | | 33.95 | | |
| 5 | 26.0 | | | 47.56 | | |
|  | 29.3 | 28.17 | 1.53 | 41.01 | 43.19 | 3.09 |
|  | 29.3 | | | 41.01 | | |
| 10 | 28.8 | | | 42.02 | | |
|  | 28.3 | 28.58 | 0.24 | 43.03 | 42.35 | 0.48 |
|  | 28.8 | | | 42.02 | | |
|  | 23.3 | | | 53.11 | | |

TABLE 9-continued

| K. K. Redda/Chavor Exp.: MCF-7 Cells | Cytoxicity on MCF-7 cells | | | | Sep. 26 to Sep. 30, 2005 | |
|---|---|---|---|---|---|---|
| Drugs | Cells (x10$^4$) | Mean | SD | % Inhibition | Mean | SD |
| 50 | 24.0 | 23.75 | 0.35 | 51.60 | 52.10 | 0.71 |
|  | 24.0 |  |  | 51.60 |  |  |
| CM-110104 | 34.0 |  |  | 31.43 |  |  |
| (µg/ml) |  |  |  |  |  |  |
| 1 | 35.0 | 34.42 | 0.42 | 29.41 | 30.59 | 0.86 |
|  | 34.3 |  |  | 30.92 |  |  |
|  | 27.5 |  |  | 44.54 |  |  |
| 5 | 28.5 | 28.08 | 0.42 | 42.52 | 43.36 | 0.86 |
|  | 28.3 |  |  | 43.03 |  |  |
|  | 28.5 |  |  | 42.52 |  |  |
| 10 | 27.0 | 27.92 | 0.66 | 45.55 | 43.70 | 1.32 |
|  | 28.3 |  |  | 43.03 |  |  |
|  | 19.8 |  |  | 60.17 |  |  |
| 50 | 20.0 | 19.87 | 0.31 | 59.66 | 60.34 | 0.63 |
|  | 19.3 |  |  | 61.18 |  |  |
| MCF-7 | Mean |  |  |  |  |  |

TABLE 10

| Drug Inhibition on PC-3 Cells | | | | |
|---|---|---|---|---|
|  | 1 | 5 | 10 | 50 |
| Drugs (µg/ml) | | | | |
| CM-091303 (µg/ml) | 27.64 | 27.72 | 26.28 | 42.86 |
| CM-090803 (µg/ml) | 25.09 | 28.57 | 29 | 36.65 |
| CM-110104 (µg/ml) | 9.1 | 36.05 | 35.8 | 48.81 |
| AZT (µg/ml) | 13.69 | 27.21 | 37.16 |  |
| SD Drugs | | | | |
| CM-091303 (µg/ml) | 2.52 | 3.39 | 3.8 | 2.16 |
| CM-090803 (µg/ml) | 1.03 | 1.1 | 1.18 | 6.24 |
| CM-110104 (µg/ml) | 6.78 | 3.09 | 2.41 | 1.80 |
| AZT (µg/ml) | 0.67 | 0.73 | 0.32 |  |

TABLE 11

| K. K. Redda/Chavor Exp.: MCF-7 Cells | Cytoxicity on MCF-7 cells | | | | Sep. 12 to Sep. 16, 2005 | |
|---|---|---|---|---|---|---|
| Drugs | Cells (x10$^4$) | Mean | SD | % Inhibition | Mean | SD |
|  | 60.5 |  |  |  |  |  |
| 2% DMSO | 55.5 | 57.67 | 2.09 | 0 |  |  |
|  | 57.0 |  |  |  |  |  |
| AZT | 44.5 |  |  | 22.83 |  |  |
| (µg/ml) |  |  |  |  |  |  |
| 1 | 46.0 | 45.25 | 0.61 | 20.23 | 21.53 | 1.06 |
|  | 45.3 |  |  | 21.53 |  |  |
|  | 30.0 |  |  | 47.98 |  |  |
| 5 | 27.8 | 28.58 | 1.01 | 51.88 | 50.43 | 1.75 |
|  | 28.0 |  |  | 51.45 |  |  |
|  | 17.5 |  |  | 69.65 |  |  |
| 10 | 21.5 | 20.17 | 1.89 | 62.72 | 65.03 | 3.27 |
|  | 21.5 |  |  | 62.72 |  |  |
| M/R-63-1 | 33.3 |  |  | 42.34 |  |  |
| (µg/ml) |  |  |  |  |  |  |
| 1 | 32.8 | 32.17 | 1.20 | 43.21 | 44.22 | 2.07 |
|  | 30.5 |  |  | 47.11 |  |  |
|  | 27.3 |  |  | 52.75 |  |  |
| 5 | 27.5 | 28.42 | 1.48 | 52.31 | 50.72 | 2.56 |
|  | 39.5 |  |  | 47.11 |  |  |
|  | 30.8 |  |  | 46.68 |  |  |

TABLE 11-continued

| K. K. Redda/Chavor Exp.: MCF-7 Cells | Cytoxicity on MCF-7 cells | | | | Sep. 12 to Sep. 16, 2005 | |
|---|---|---|---|---|---|---|
| Drugs | Cells (x10$^4$) | Mean | SD | % Inhibition | Mean | SD |
| 10 | 29.3 | 29.25 | 1.22 | 49.28 | 49.28 | 2.12 |
|  | 27.8 |  |  | 51.88 |  |  |
|  | 24.3 |  |  | 57.95 |  |  |
| 50 | 23.5 | 23.58 | 0.51 | 59.25 | 59.10 | 0.89 |
|  | 23.0 |  |  | 60.12 |  |  |
| M/R-67 | 39.3 |  |  | 31.94 |  |  |
| (µg/ml) |  |  |  |  |  |  |
| 1 | 38.8 | 39.67 | 0.96 | 32.80 | 31.21 | 1.67 |
|  | 41.0 |  |  | 28.90 |  |  |
|  | 38.3 |  |  | 33.67 |  |  |
| 5 | 37.5 | 37.67 | 0.42 | 34.97 | 34.68 | 0.74 |
|  | 37.3 |  |  | 35.40 |  |  |
|  | 36.0 |  |  | 37.67 |  |  |
| 10 | 35.8 | 35.17 | 1.01 | 38.01 | 39.02 | 1.75 |
|  | 33.8 |  |  | 41.47 |  |  |
|  | 30.5 |  |  | 47.11 |  |  |
| 50 | 31.5 | 30.60 | 0.82 | 45.8 | 47.11 | 1.42 |
|  | 29.5 |  |  | 48.84 |  |  |
| M/R-64-1 | 30.8 |  |  | 46.68 |  |  |
| (µg/ml) |  |  |  |  |  |  |
| 1 | 27.5 | 29.08 | 1.33 | 52.31 | 49.57 | 2.30 |
|  | 29.0 |  |  | 49.71 |  |  |
|  | 29.0 |  |  | 49.71 |  |  |
| 5 | 28.0 | 29.00 | 0.82 | 51.45 | 49.71 | 1.42 |
|  | 30.0 |  |  | 47.98 |  |  |
|  | 27.0 |  |  | 53.18 |  |  |
| 10 | 30.0 | 29.08 | 1.48 | 47.98 | 49.57 | 2.56 |
|  | 30.3 |  |  | 47.54 |  |  |
|  | 29.8 |  |  | 48.41 |  |  |
| 50 | 28.0 | 29.00 | 0.74 | 51.46 | 49.71 | 1.28 |
|  | 29.3 |  |  | 49.28 |  |  |
| M/R-68-1 | 50.3 |  |  | 12.86 |  |  |

TABLE 12

| Drug Inhibition on MCF-7 Cells | | | | |
|---|---|---|---|---|
|  | 1 | 5 | 10 | 50 |
| Drugs (µg/ml) | | | | |
| CM-091303 (µg/ml) | 27.06 | 27.9 | 39.16 | 47.23 |
| CM-090803 (µg/ml) | 32.77 | 43.19 | 42.35 | 52.10 |
| CM-110104 (µg/ml) | 30.59 | 43.36 | 43.7 | 60.34 |
| AZT (µg/ml) | 26.55 | 46.86 | 65.21 |  |
| SD Drugs | | | | |
| CM-091303 (µg/ml) | 1.19 | 1.43 | 1.95 | 1.04 |
| CM-090803 (µg/ml) | 0.86 | 3.09 | 0.48 | 0.71 |
| CM-110104 (µg/ml) | 0.86 | 0.86 | 1.32 | 0.63 |
| AZT (µg/ml) | 1.32 | 2.22 | 1.63 |  |

TABLE 13

| K. K. Redda/Chavor Exp.: MCF-7 Cells | Cytoxicity on MCF-7 cells | | | | Sep. 08 to Sep. 12, 2005 | |
|---|---|---|---|---|---|---|
| Drugs | Cells (x10$^4$) | Mean | SD | % Inhibition | Mean | SD |
|  | 74.3 |  |  |  |  |  |
| 2% DMSO | 68.5 | 70.50 | 2.65 | 0 |  |  |
|  | 68.8 |  |  |  |  |  |
| AZT | 51.0 |  |  | 27.66 |  |  |
| (µg/ml) |  |  |  |  |  |  |
| 1 | 53.8 | 52.33 | 1.12 | 23.76 | 25.77 | 1.59 |
|  | 52.3 |  |  | 25.89 |  |  |
|  | 42.3 |  |  | 40.07 |  |  |

TABLE 13-continued

| | | | | | | |
|---|---|---|---|---|---|---|
| 5 | 42.3 | 42.75 | 0.71 | 40.07 | 39.36 | 1.00 |
| | 43.8 | | | 37.94 | | |
| | 30.0 | | | 57.45 | | |
| 10 | 30.0 | 30.00 | 0.00 | 57.45 | 57.45 | 0.00 |
| | 30.0 | | | 57.45 | | |
| M/R-67 | 46.8 | | | 33.69 | | |
| (µg/ml) | | | | | | |
| 1 | 43.8 | 44.92 | 1.31 | 37.94 | 36.29 | 1.86 |
| | 44.3 | | | 37.23 | | |
| | 41.8 | | | 40.78 | | |
| 5 | 37.0 | 39.75 | 2.01 | 47.52 | 43.62 | 2.85 |
| | 40.5 | | | 42.55 | | |
| | 33.3 | | | 52.84 | | |
| 10 | 34.8 | 34.33 | 0.77 | 50.71 | 51.30 | 1.10 |
| | 35.0 | | | 50.35 | | |
| | 38.5 | | | 45.39 | | |
| 50 | 41.8 | 40.67 | 1.53 | 40.78 | 42.32 | 2.17 |
| | 41.8 | | | 40.78 | | |
| M/R-68-1 | 62.3 | | | 11.70 | | |
| (µg/ml) | | | | | | |
| 1 | 55.8 | 59.75 | 2.86 | 20.92 | 15.25 | 4.05 |
| | 61.3 | | | 13.12 | | |
| | 51.0 | | | 27.66 | | |
| 5 | 44.3 | 47.92 | 2.79 | 37.23 | 32.03 | 3.95 |
| | 48.5 | | | 31.21 | | |
| | 49.5 | | | 29.79 | | |
| 10 | 51.0 | 51.42 | 1.76 | 27.66 | 27.07 | 2.50 |
| | 53.8 | | | 23.76 | | |
| | 38.8 | | | 45.04 | | |
| 50 | 36.3 | 38.92 | 2.25 | 48.58 | 44.80 | 3.19 |
| | 41.8 | | | 40.78 | | |

| Drugs (µg/ml) | Mean 0 | 1 | 5 | 10 | 50 |
|---|---|---|---|---|---|
| MCF-7 | | | | | |
| AZT | | 25.77 | 39.36 | 57.45 | |
| M/R-67 | | 36.29 | 43.62 | 51.3 | 42.32 |
| M/R-68-1 | | 15.25 | 32.03 | 27.07 | 44.80 |
| SD | | | | | |
| AZT | | 1.59 | 1 | 0 | |
| M/R-67 | | 1.86 | 2.85 | 1.1 | 2.17 |

TABLE 14

Drug inhibition on MCF-7 Cells

| | | | | | | |
|---|---|---|---|---|---|---|
| 1 | 54.0 | 50.75 | 2.47 | 6.36 | 11.99 | 4.29 |
| | 48.0 | | | 16.76 | | |
| | 37.5 | | | 34.97 | | |
| 5 | 40.8 | 39.33 | 1.36 | 29.34 | 31.79 | 2.36 |
| | 39.8 | | | 31.07 | | |
| | 36.3 | | | 37.14 | | |
| 10 | 33.8 | 34.83 | 1.05 | 41.47 | 39.60 | 1.82 |
| | 34.5 | | | 40.17 | | |
| | 31.3 | | | 45.81 | | |
| 50 | 32.5 | 31.92 | 0.51 | 43.64 | 44.65 | 0.89 |
| | 32.0 | | | 44.51 | | |

| Drugs (µg/ml) | Mean 0 | 1 | 5 | 10 | 50 |
|---|---|---|---|---|---|
| MCF-7 | | | | | |
| M/R-67 | | 31.21 | 34.68 | 39.02 | 47.11 |
| M/R-64-1 | | 49.57 | 49.71 | 49.57 | 49.71 |
| M/R-68-1 | | 11.99 | 31.79 | 39.6 | 44.65 |
| M/R-63-1 | | 44.22 | 50.72 | 49.28 | 59.10 |
| AZT | | 21.53 | 50.43 | 65.03 | |
| SD | | | | | |
| M/R-67 | | 1.67 | 0.74 | 1.75 | 1.42 |
| M/R-64-1 | | 2.3 | 1.42 | 2.56 | 1.28 |
| M/R-68-1 | | 4.29 | 2.36 | 1.82 | 0.89 |

TABLE 14-continued

Drug inhibition on MCF-7 Cells

| M/R-63-1 | 2.07 | 2.56 | 2.12 | 0.89 |
|---|---|---|---|---|
| AZT | 1.06 | 1.56 | 3.27 | |

TABLE 15

| M/R-68-1 | 4.05 | 3.95 | 2.5 | 3.19 |
|---|---|---|---|---|

TABLE 16

K. K. Redda/Chavor Exp.: MCF-7 Cells — Cytoxicity on MCF-7 cells — Dec. 12 to Dec. 16, 2005

| Drugs | Cells (×10⁴) | Mean | SD | % Inhibition | Mean | SD |
|---|---|---|---|---|---|---|
| 2% DMSO | 50.3 | 50.92 | 0.77 | 0 | | |
| | 52.0 | | | | | |
| | 50.5 | | | | | |
| AZT | 43.3 | | | 15.06 | | |
| (µg/ml) | | | | | | |
| 1 | 43.3 | 43.08 | 0.24 | 15.06 | 15.38 | 0.46 |
| | 42.8 | | | 16.04 | | |
| | 31.5 | | | 38.13 | | |
| 5 | 32.3 | 32.08 | 0.42 | 36.66 | 36.99 | 0.83 |
| | 32.5 | | | 36.17 | | |
| | 22.0 | | | 56.79 | | |
| 10 | 25.5 | 24.08 | 1.50 | 49.92 | 52.70 | 2.96 |
| | 24.8 | | | 51.39 | | |
| CHCl 3M | 54.0 | | | −6.06 | | |
| (µg/ml) | | | | | | |
| 1 | 54.3 | 53.17 | 1.36 | −6.55 | −4.42 | 2.67 |
| | 51.3 | | | −0.65 | | |
| | 53.8 | | | −5.56 | | |
| 5 | 51.5 | 52.75 | 0.94 | −1.15 | −3.60 | 1.84 |
| | 50.0 | | | −4.09 | | |
| | 42.5 | | | 16.53 | | |
| 10 | 43.3 | 43.75 | 1.27 | 15.06 | 14.08 | 2.50 |
| | 45.5 | | | 10.64 | | |
| | 32.0 | | | 37.15 | | |
| 50 | 32.8 | 31.50 | 1.27 | 35.68 | 38.13 | 2.50 |
| | 29.8 | | | 41.57 | | |
| CHNM 3M | 44.3 | | | 13.09 | | |
| (µg/ml) | | | | | | |
| 1 | 45.0 | 44.50 | 0.35 | 11.62 | 12.60 | 0.69 |
| | 44.3 | | | 13.09 | | |
| | 25.8 | | | 49.43 | | |
| 5 | 24.0 | 24.75 | 0.74 | 52.86 | 51.39 | 1.45 |
| | 24.5 | | | 51.88 | | |
| | 5.0 | | | 90.18 | | |
| 10 | 4.8 | 4.92 | 0.12 | 90.67 | 90.34 | 0.23 |
| | 5.0 | | | 90.18 | | |
| | 1.8 | | | 96.56 | | |
| 50 | 2.0 | 1.75 | 0.20 | 96.07 | 96.56 | 0.40 |
| | 1.5 | | | 97.05 | | |

| Drugs (µg/ml) | 1 | 5 | 10 | 50 |
|---|---|---|---|---|
| MCF-7 | | | | |
| CHCl 3M | −4.42 | −3.6 | 14.08 | 38.13 |
| CHNM 3M | 12.6 | 51.39 | 90.34 | 96.66 |
| AZT | 15.38 | 36.99 | 52.7 | |
| SD | | | | |
| CHCl 3M | 2.67 | 1.84 | 2.5 | 2.50 |
| CHNM 3M | 0.69 | 1.45 | 0.23 | 0.40 |
| AZT | 0.46 | 0.83 | 2.96 | |

Examining the response of the synthesized compounds to MCF-7 cells in the different drug concentrations reveals that the compounds of the invention, in particular the three (code: CHBr2M, CHCl2M and CHNM3M) show good activities.

Figure 2:
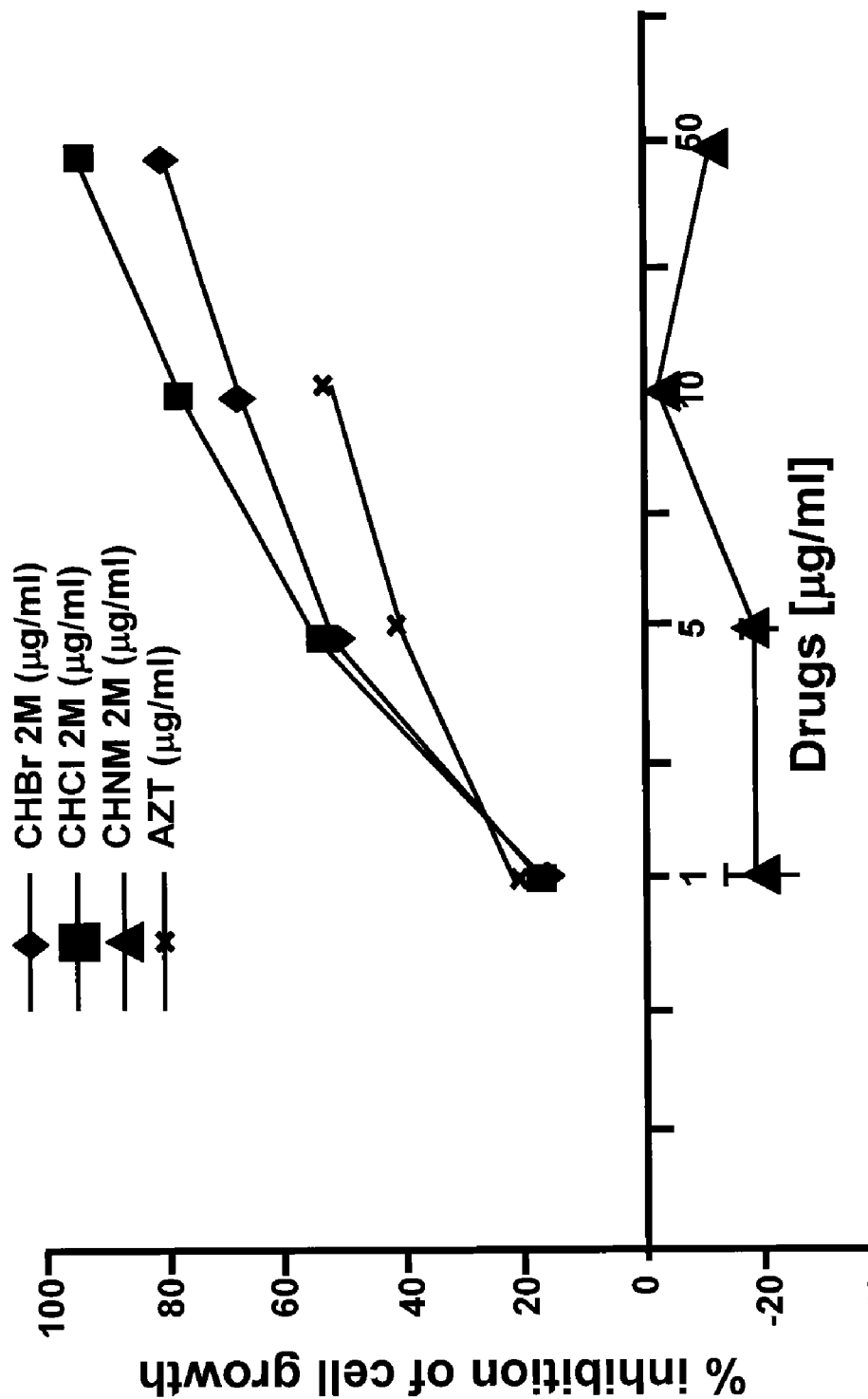
Figure 3:
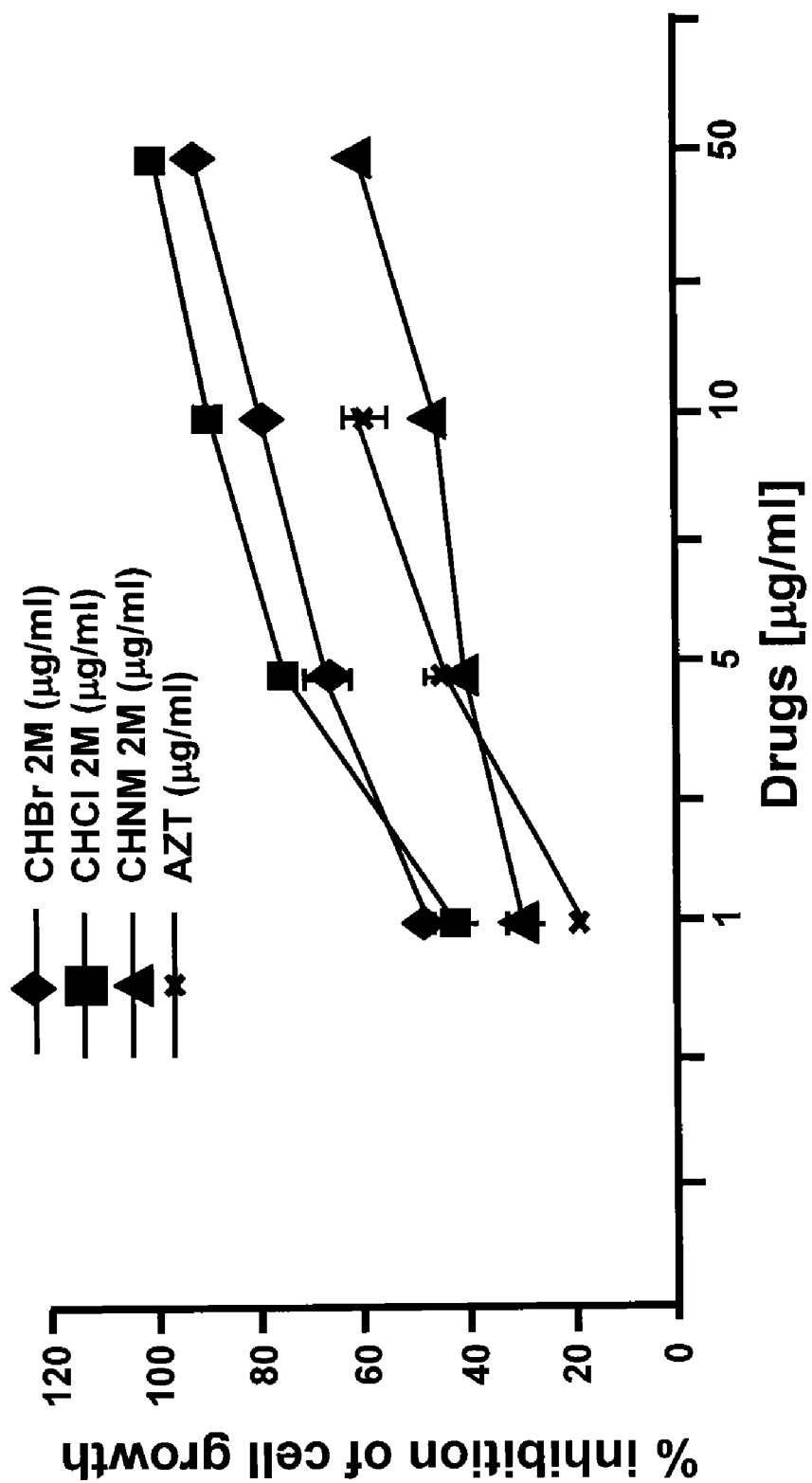
Figure 4A:
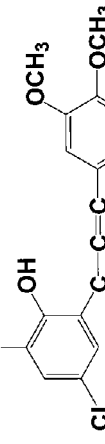
Figure 5:
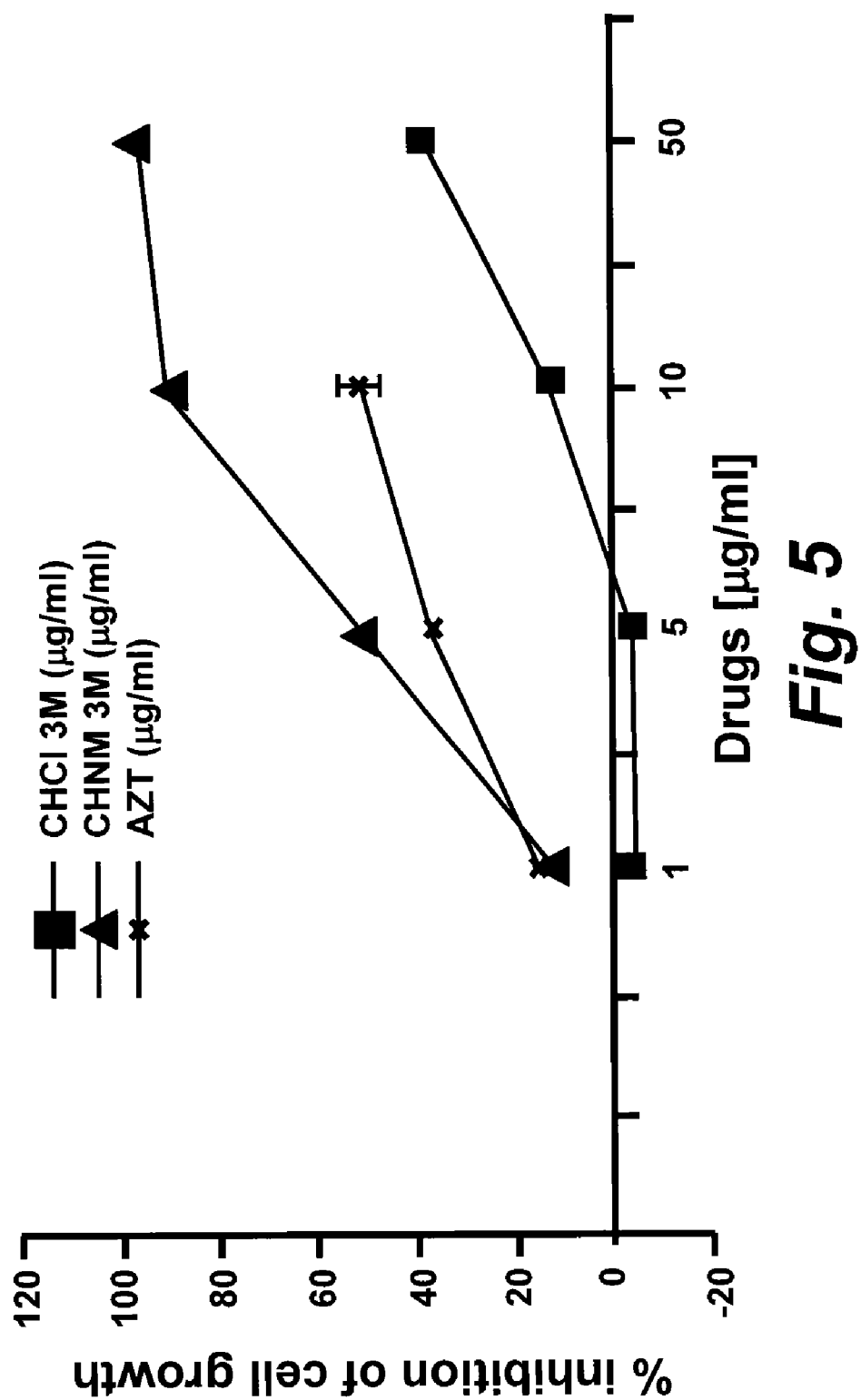
FIG. 5 is a graph illustrating drug inhibition on MCF-7 cells by CHCl 3M, CHNM 3M, and AZT.
Figure 6:
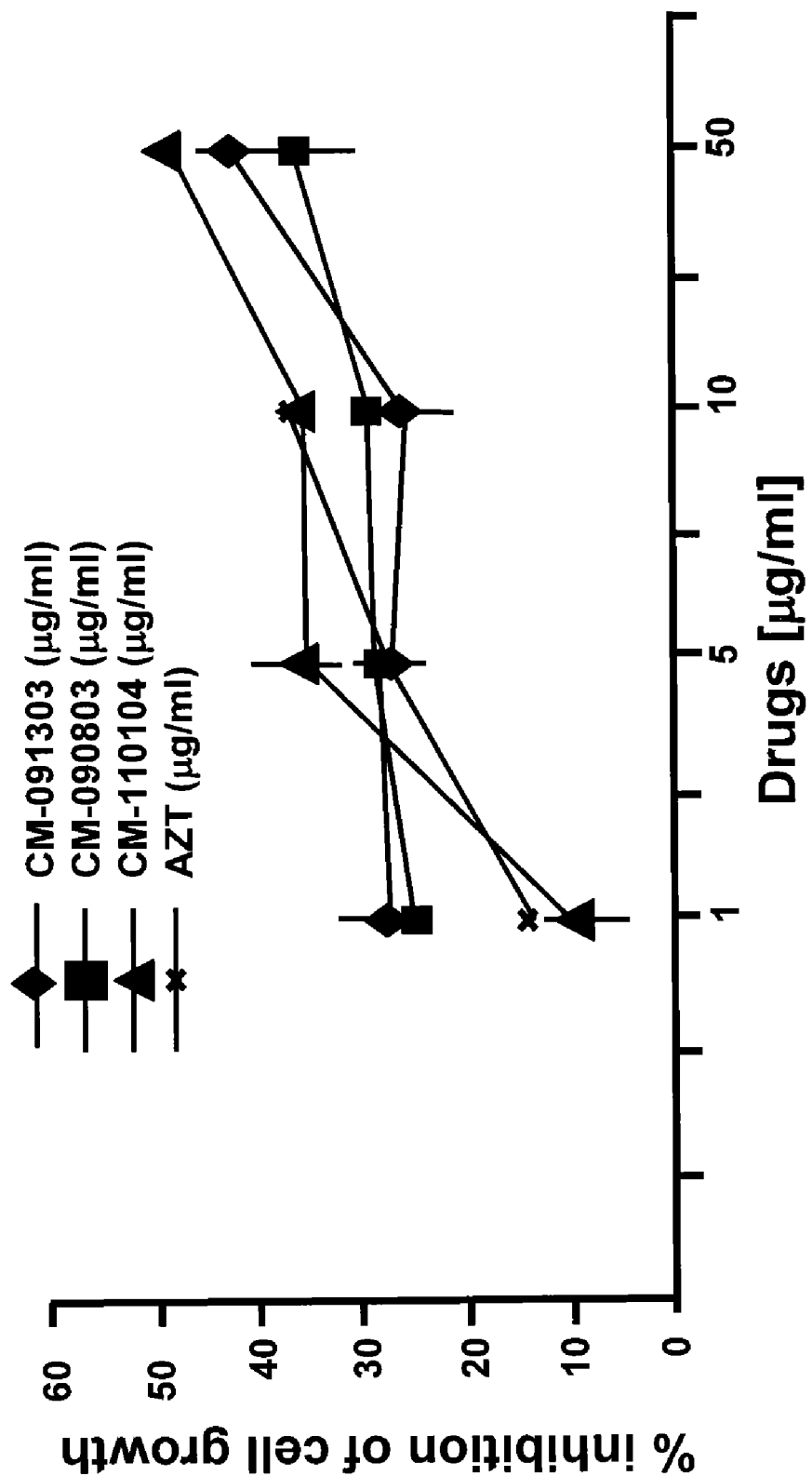
FIG. 6 is a graph illustrating drug inhibition on PC-3 cells by CM-091303, CM-090803, CM-110104, and AZT.
Figure 7:
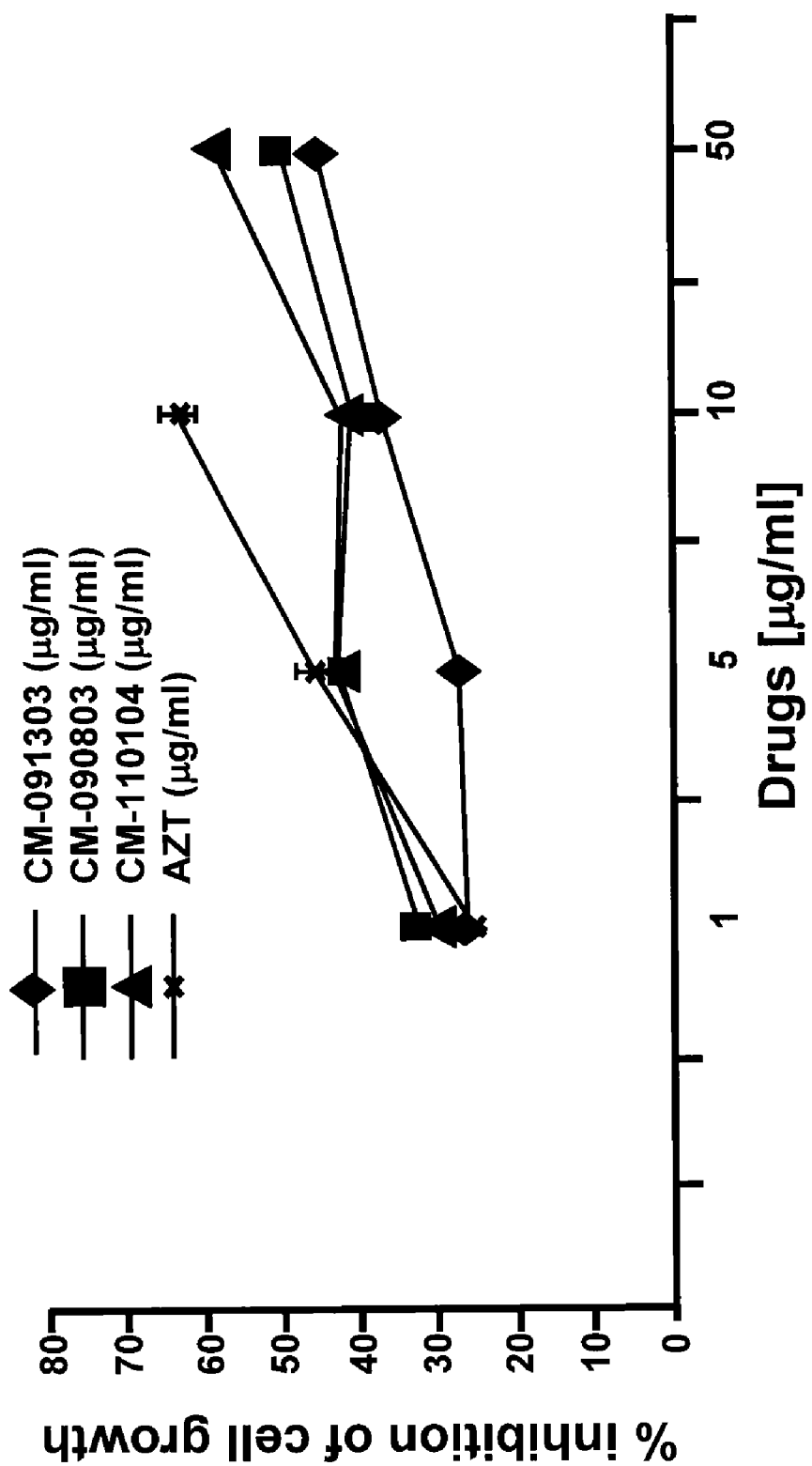
FIG. 7 is a graph illustrating drug inhibition on MCF-7 cells by CM-091303, CM-090803, CM-110104, and AZT.
Figure 8:
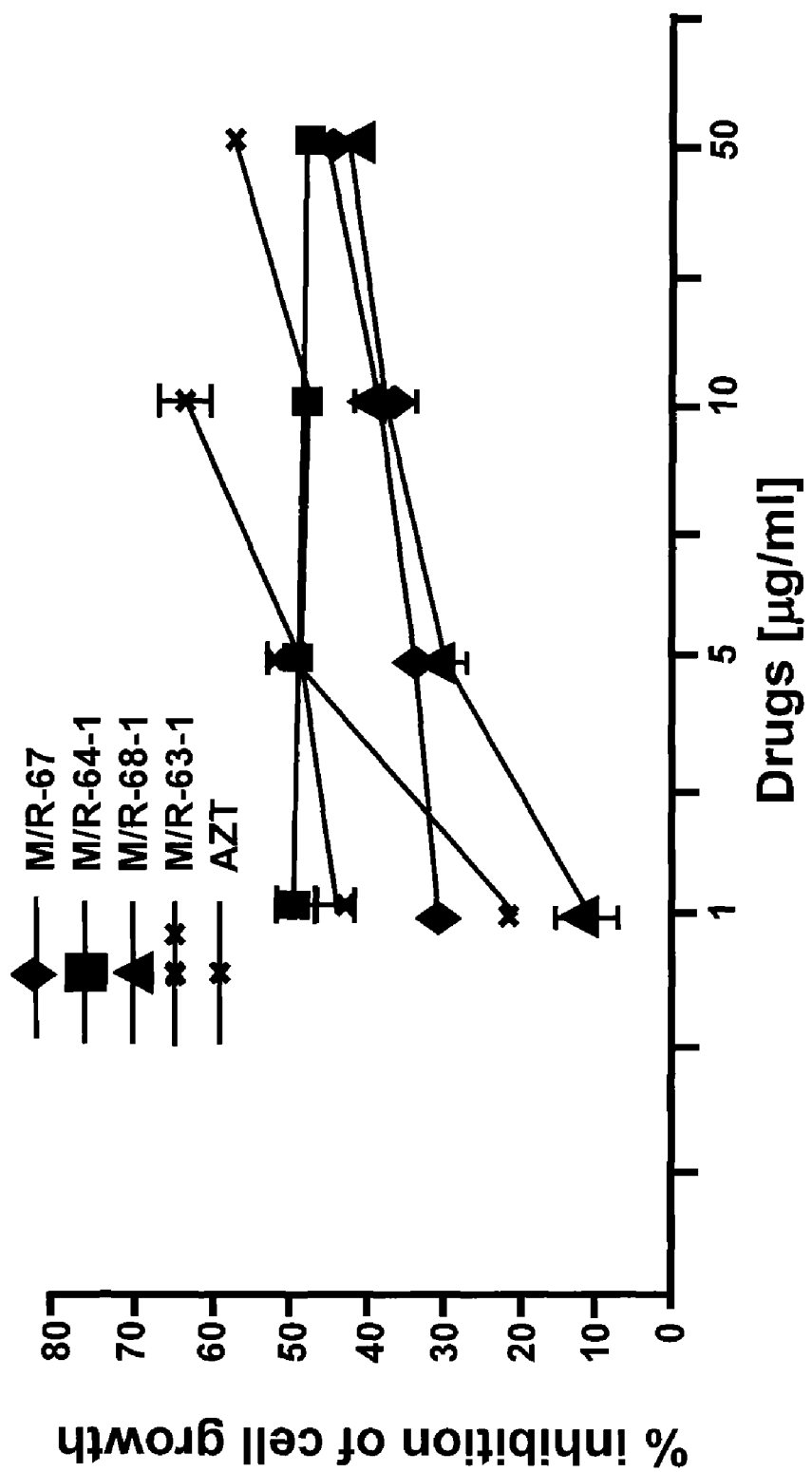
FIG. 8 is a graph illustrating drug inhibition on MCF-7 cells by M/R-67, M/R-64-1, M/R-68-1, M/R-63-1, and AZT.
Figure 9:
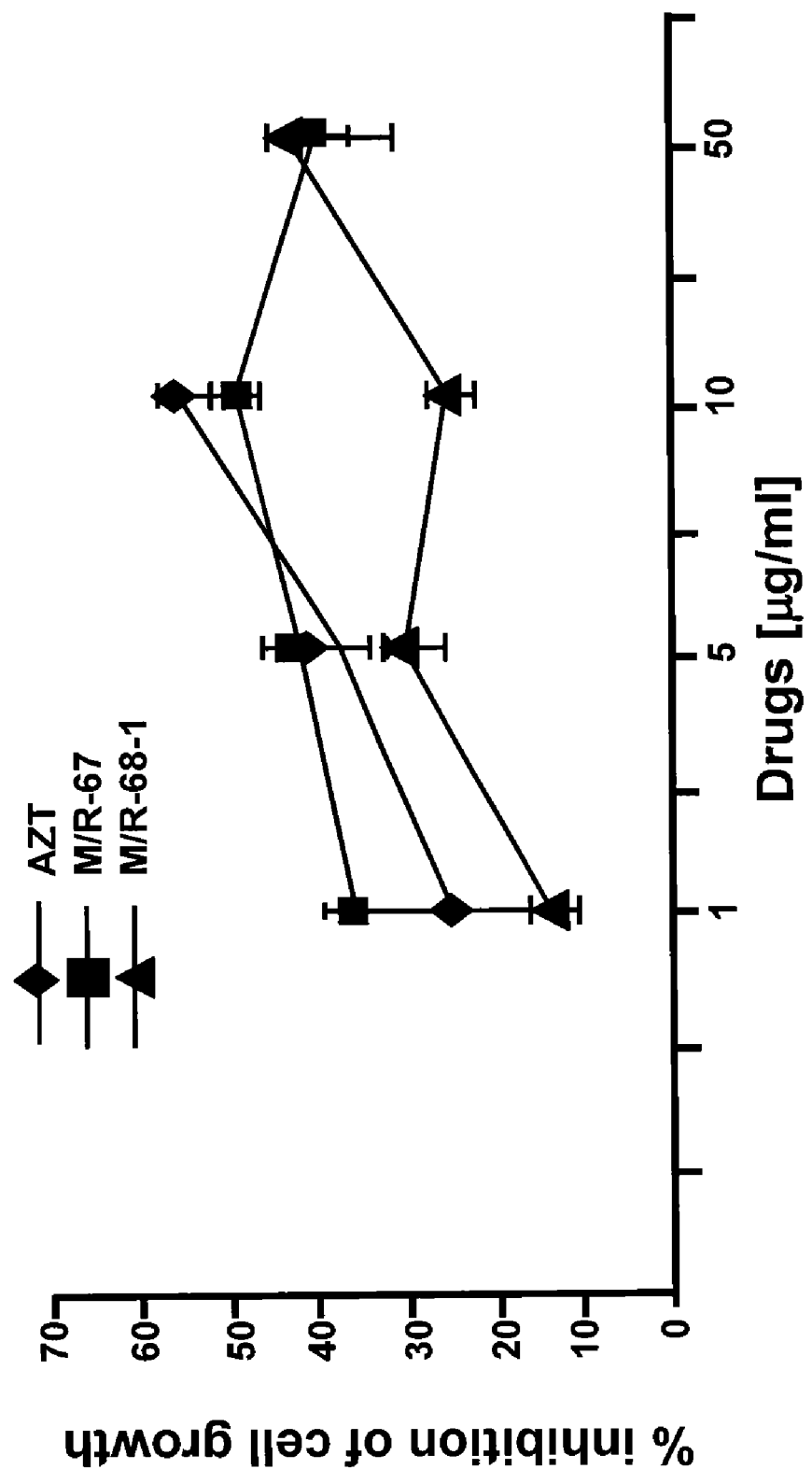
FIG. 9 is a graph illustrating drug inhibition on MCF-7 cells by AZT, M/R-67, and M/R-68-1.

These three congeners were further evaluated in H9 and PC3 cells. AZT was employed as a positive control in all of these experiments. These data are summarized in FIGS. 1-3. The results show that the compounds of the invention, in particular the two [CHBr2M and CHCl2M] are as good or somewhat better in inhibiting the growth in all the cultures employed.

It has been demonstrated previously that the above disclosed tests are indicative of anti-viral, anti-retroviral and, in particular, anti-HIV properties. See Mehta R, Lansky, Eur J Cancer Prev. 2004 August;13(4):345-8; Pei-Lin Wu , Yu-Lin Hsu , Tian-Shung Wu , K Bastow , Kuo-Hsiung Lee, "Kalanchosides A-C, New Cytotoxic Bufadienolides from the Aerial Parts of Kalanchoe gracilis", Org Lett. 2006 Nov. 9;8 (23): 5207-5210 17078679; Casini et al, Environmental Health Perspectives, vol. 1 10, pp801-805 (2002) and Bioorg Med Chem. 2001 November;9(11):2871-84.

The invention claimed is:

1. A compound having the structure:

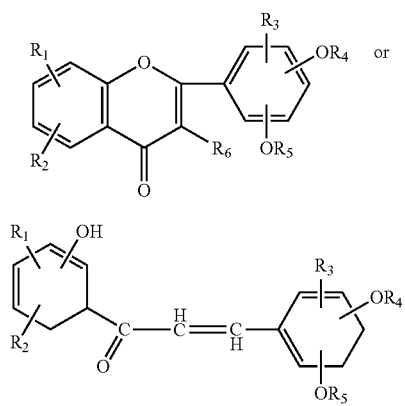

wherein:
$R_1$ is an electronegative substituent,
$R_2$ is $R_1$ or alkyl,
$R_3$ is H or O-alkyl,
$R_4$ and $R_5$ are the same or different and are alkyl and
$R_6$ is H or OH.

2. A biocompatible compound of claim 1.

3. A compound of claim 2 effective against breast and/or prostate cancer.

4. A compound of claim 1 wherein said electronegative substituent is halogen or $NO_2$.

5. A compound of claim 4 wherein said electronegative substituent is Cl or Br.

6. A compound of claim 1 wherein $R_4$ and $R_5$ are each $CH_3$.

7. A compound of claim 6 having structure wherein $R_1$ and $R_2$ are each Cl and $R_3$ is $OCH_3$.

8. A compound of claim 6 having structure wherein $R_1$ and $R_2$ are each Br and $R_3$ is $OCH_3$.

9. A compound of claim 6 having structure wherein $R_1$ is $NO_2$, $R_2$ is $CH_3$ and $R_3$ is $OCH_3$.

10. A compound of claim 6 having structure wherein $R_1$ and $R_2$ are each Cl and $R_3$ is H.

11. A compound of claim 6 having structure wherein $R_1$ and $R_2$ are each Br and $R_3$ is H.

12. A compound of claim 6 having structure wherein $R_1$ is $NO_2$, $R_2$ is $CH_3$ and $R_3$ is H.

13. A compound of claim 6 having structure wherein $R_6$ is OH, $R_1$ and $R_2$ are each Cl and $R_3$ is $OCH_3$.

14. A compound of claim 6 having structure wherein $R_6$ is OH, $R_1$ and $R_2$ are each Br and $R_3$ is $OCH_3$.

15. A compound of claim 6 having structure wherein $R_6$ is OH, $R_1$ is $NO_2$, R2 is $CH_3$ and $R_3$ is $OCH_3$.

16. A compound of claim 6 having structure wherein $R_6$ is OH, $R_1$ and $R_2$ are each Cl and $R_3$ is H.

17. A compound of claim 6 having structure wherein $R_6$ is OH, $R_1$ and $R_2$ are each Br and $R_3$ is H.

18. A compound of claim 6 having structure wherein $R_6$ is OH, $R_1$ is $NO_2$, $R_2$ is $CH_3$ and $R_3$ is H.

19. A compound of claim 6 having structure wherein $R_6$ is H; $R_1$ and $R_2$ are each Cl and $R_3$ is $OCH_3$.

20. A compound of claim 6 having structure wherein $R_6$ is H; $R_1$ and $R_2$ are each Br and $R_3$ is $OCH_3$.

21. A compound of claim 6 having structure wherein $R_6$ is H; $R_1$ is $NO_2$, $R_2$ is $CH_3$ and $R_3$ is $OCH_3$.

22. A compound of claim 6 having structure wherein $R_6$ is H; $R_1$ and $R_2$ are each Cl and $R_3$ is H.

23. A compound of claim 6 having structure wherein $R_6$ is H; $R_1$ and $R_2$ are each Br and $R_3$ is H.

24. A compound of claim 6 having structure wherein $R_6$ is H; $R_1$ is $NO_2$, $R_2$ is $CH_3$ and $R_3$ is H.

25. A pharmaceutical composition comprising a therapeutically effective amount of at least one compound of claim 2 and a pharmaceutically acceptable carrier or excipient.

26. A composition of claim 25 effective for the treatment of an HIV infection.

27. A composition of claim 25 additionally containing at least one biologically active agent different from said at least one compound, wherein said biologically active agent is an anti-HIV agent.

28. A method for the treatment of a mammal in need of anti-breast cancer and/or anti-prostate cancer, or anti-HIV therapy, comprising administering thereto a therapeutically effective amount of at least one compound of claim 2.

29. A method of claim 28 comprising additionally administering to said mammal at least one biologically active agent different from said at least one compound, wherein said biologically active agent is an anti-HIV agent.

30. An article of manufacture comprising packaging material and at least one therapeutic agent contained within said packaging material, wherein said at least one therapeutic agent is effective for the treatment of a subject in need of anti-breast cancer therapy and/or anti-prostate cancer therapy, or anti-HIV therapy, and wherein said packaging material comprises a label which indicates that said therapeutic agent can be used for at least ameliorating the symptoms with which said subject is afflicted, and wherein said at least one therapeutic agent is a compound of claim 2.

31. The article of claim 30 wherein said packaging material additionally contains a biologically active agent different from said at least one compound, wherein said biologically active agent is an anti-HIV agent.

32. A method for the synthesis of a chalcone of claim 1 by the Claisen condensation of an acetophenone and a benzaldehyde.

33. A method for the synthesis of a flavone of claim 1 by a three step BakerVenkataraman rearrangement.

* * * * *

UNITED STATES PATENT AND TRADEMARK OFFICE
CERTIFICATE OF CORRECTION

PATENT NO. : 8,314,143 B2
APPLICATION NO. : 11/968146
DATED : November 20, 2012
INVENTOR(S) : Kinfe Redda, Chavonda Janeebra Mills and Nelly Mateeva It is certified that error appears in the above-identified patent and that said Letters Patent is hereby corrected as shown below:

In the Specification

Column 1, line 5, please insert

--This invention was made with government support under RCMI G12 RR 03020 grant awarded by the National Institutes of Health. The government has certain rights in the invention.--

Signed and Sealed this
Twenty-seventh Day of October, 2015

Michelle K. Lee
*Director of the United States Patent and Trademark Office*